United States Patent
Freer et al.

(10) Patent No.: US 11,517,240 B2
(45) Date of Patent: Dec. 6, 2022

(54) NON-CONTACT BODY AND HEAD BASED MONITORING OF BRAIN ELECTRICAL ACTIVITY

(71) Applicant: Freer Logic, Inc., Skyland, NC (US)

(72) Inventors: Peter Anthony Freer, Fletcher, NC (US); Gwen Kathryn Freer, Fletcher, NC (US)

(73) Assignee: Freer Logic, Inc., Skyland, NC (US)

( * ) Notice: Subject to any disclaimer, the term of this patent is extended or adjusted under 35 U.S.C. 154(b) by 46 days.

(21) Appl. No.: 15/497,734

(22) Filed: Apr. 26, 2017

(65) Prior Publication Data
US 2017/0311831 A1    Nov. 2, 2017

Related U.S. Application Data

(60) Provisional application No. 62/329,259, filed on Apr. 29, 2016.

(51) Int. Cl.
*A61B 5/316* (2021.01)
*A61B 5/11* (2006.01)
(Continued)

(52) U.S. Cl.
CPC .............. *A61B 5/316* (2021.01); *A61B 5/11* (2013.01); *A61B 5/1123* (2013.01); *A61B 5/16* (2013.01);
(Continued)

(58) Field of Classification Search
None
See application file for complete search history.

(56) References Cited

U.S. PATENT DOCUMENTS 3,544,162 A * 12/1970 Uchiyamada .......... B60N 2/818
297/410
3,951,134 A *  4/1976 Malech ................ A61B 5/0476
600/544
(Continued)

FOREIGN PATENT DOCUMENTS

JP    2008-525063 A    7/2008
JP    2011-019845 A    2/2011
(Continued)

OTHER PUBLICATIONS

Fong, B., Harvey, M., Lagoutchev, K. "Portable EEG Recording Using a Lock-In Amplifier". Pertinent pp. 4-7. (Year: 2014).*
(Continued)

*Primary Examiner* — Allen Porter
*Assistant Examiner* — Samuel C Kim
(74) *Attorney, Agent, or Firm* — Oblon, McClelland, Maier & Neustadt, L.L.P.

(57) ABSTRACT

Apparatus and methods for monitoring electrical activity within the brain of a person ("brainwaves") employing electrodes or other sensors placed proximate to portions of the body below the head to develop raw signals without physically touching the body and penetrating hair and clothing. Additionally, apparatus and methods for monitoring electrical activity within the brain of a person ("brainwaves") employing non-contacting sensors placed proximate to portions of the head to develop raw signals. The raw signals are filtered to produce analysis signals including frequency components relevant to brain electrical activity while attenuating unrelated frequency components. The apparatus and methods can be used for biofeedback-based attention training, human performance training, gaming, biometrics, cognitive state detection, and relaxation training. Either wired or wireless signal connections are made to (Continued)

electronic circuitry, typically including a digital computer, for performing signal processing and analysis functions.

30 Claims, 17 Drawing Sheets

(51) Int. Cl.
  *A61B 5/16* (2006.01)
  *A61B 5/18* (2006.01)
  *A61B 5/291* (2021.01)
  *A61B 5/374* (2021.01)
  *A61B 5/00* (2006.01)

(52) U.S. Cl.
  CPC ............... *A61B 5/18* (2013.01); *A61B 5/291* (2021.01); *A61B 5/374* (2021.01); *A61B 5/165* (2013.01); *A61B 5/6893* (2013.01); *A61B 2503/22* (2013.01)

(56) References Cited

U.S. PATENT DOCUMENTS

| | | | |
|---|---|---|---|
| 5,458,142 A * | 10/1995 | Farmer | A61N 2/02 600/409 |
| 5,808,552 A * | 9/1998 | Wiley | A61B 5/11 340/562 |
| 5,813,993 A * | 9/1998 | Kaplan | A61B 5/7203 600/26 |
| 6,073,039 A * | 6/2000 | Berson | A61B 5/04085 600/372 |
| 6,097,981 A | 8/2000 | Freer | |
| 6,402,520 B1 | 6/2002 | Freer | |
| 6,493,576 B1 * | 12/2002 | Dankwart-Eder | A61B 5/38 600/544 |
| 6,626,676 B2 | 9/2003 | Freer | |
| 8,391,967 B2 * | 3/2013 | Freer | A61B 5/0002 600/544 |
| 2004/0230549 A1 | 11/2004 | Freer et al. | |
| 2006/0058694 A1 * | 3/2006 | Clark | G01R 29/12 600/509 |
| 2008/0015801 A1 * | 1/2008 | Sharma | A61B 5/05 702/77 |
| 2008/0275358 A1 | 11/2008 | Freer et al. | |
| 2009/0299210 A1 * | 12/2009 | Marcarian | A61B 5/4561 600/595 |
| 2009/0318827 A1 | 12/2009 | Freer et al. | |
| 2010/0152600 A1 * | 6/2010 | Droitcour | A61B 5/05 600/534 |
| 2010/0234752 A1 * | 9/2010 | Sullivan | A61B 5/04842 600/544 |
| 2010/0245091 A1 | 9/2010 | Singh et al. | |
| 2011/0043225 A1 * | 2/2011 | Sullivan | A61B 5/04004 324/658 |
| 2012/0004523 A1 | 1/2012 | Richter et al. | |
| 2012/0203131 A1 | 8/2012 | Dilorenzo | |
| 2012/0232410 A1 * | 9/2012 | Freer | A61B 5/0002 600/483 |
| 2012/0245481 A1 * | 9/2012 | Blanco | A61B 5/7264 600/544 |
| 2012/0265080 A1 * | 10/2012 | Yu | A61B 5/04 600/484 |
| 2015/0005608 A1 * | 1/2015 | Evans | A61B 5/0428 600/383 |
| 2015/0038869 A1 | 2/2015 | Simon et al. | |
| 2015/0105641 A1 * | 4/2015 | Austin | A61B 5/18 600/364 |
| 2015/0133804 A1 * | 5/2015 | Sugiyama | A61B 5/0408 600/509 |
| 2016/0029946 A1 * | 2/2016 | Simon | A61B 5/4088 600/544 |

FOREIGN PATENT DOCUMENTS

| | | | | |
|---|---|---|---|---|
| JP | 2015-046103 A | 3/2015 | | |
| WO | WO 2004/089209 A1 | 10/2004 | | |
| WO | WO 2015/034065 A1 | 3/2015 | | |
| WO | WO-2016115982 A1 * | 7/2016 | ............ | G06F 3/012 |

OTHER PUBLICATIONS

International Search Report and Written Opinion dated Jul. 26, 2017 in PCT/US17/29675.
Office Action issued in corresponding Japanese Patent Application No. 2018-556448 dated Apr. 2, 2021 (with English translation) (11 pages).
Office Action issued in corresponding Japanese Patent Application No. 2018-556448 dated Feb. 25, 2022 (with English translation) 4 pages.
Office Action issued in corresponding Japanese Patent Application No. 2018-556448US dated Aug. 30, 2022 (with English translation).

* cited by examiner

NON-CONTACT BODY AND HEAD BASED MONITORING OF BRAIN ELECTRICAL ACTIVITY

INCORPORATION BY REFERENCE

This present disclosure claims the benefit of U.S. Provisional Application No. 62/329,259, "Non-Contact Body and Head-Based Monitoring of Brain Electrical Activity" filed on Apr. 29, 2016, which is incorporated herein by reference in its entirety.

BACKGROUND

The background description provided herein is for the purpose of generally presenting the context of the disclosure. Work of the presently named inventors, to the extent the work is described in this background section, as well as aspects of the description that may not otherwise qualify as prior art at the time of filing, are neither expressly nor impliedly admitted as prior art against the present disclosure.

The term electroencephalography (EEG) generally refers to the measurement of electrical activity produced by the brain as measured or recorded from electrodes placed on the scalp of a person. The resultant electrical signals from the electrodes are correspondingly termed EEG signals, and are based on the electrical activity within the brain of a person. Such electrical activity is commonly termed "brainwave" activity. A related term, electroencephalogram, refers to a graphic record produced by an EEG.

A system for naming points on the scalp or head where EEG electrodes are attached has been developed. Thus, the International "10-20" system is widely used to describe the location of EEG scalp electrodes for standardization. The 10-20 system is based on the surface placement of the electrode and its relationship to the underlying area of cerebral cortex. The "10" and "20" refer to the actual distances between adjacent electrodes as either 10% or 20% of the total front-back or right-left distance of the skull. Further, the letters F, T, C, P and O, which stand for Frontal, Temporal, Central, Parietal and Occipital, respectively, are used to identify the lobe over which the sensor is placed. A number is further used to identify the hemisphere location. Even numbers (2, 4, 6, 8) refer to electrode positions on the right hemisphere, and odd numbers (1, 3, 5, 7) refer to electrode positions on the left hemisphere.

SUMMARY

Aspects of the disclosure relate to a monitoring of electrical activity within a brain or body of a person acquired from a distance without contact to the brain or body of the person for purposes such as, but not limited to, biofeedback-based attention training, monitoring cognitive state, monitoring emotions, monitoring drowsiness, monitoring stress, monitoring cognitive load, human performance training, gaming, and relaxation training.

Aspect of the disclosure may provide a non-contact electroencephalography (EEG) device for monitoring electrical activity generated by a brain of a person. The device can include a non-contact sensor that can be configured to detect electrical signals that include electrical signals produced by the brain of the person without making contact with the person. The device may further include an amplifying device coupled to the non-contacting sensor that is configured to generate analysis signals corresponding to the electrical activity generated by the brain of the person in proximity to the non-contacting sensor by attenuating frequency components of the detected electrical signals that are unrelated to the analysis signals, while amplifying frequency components of the detected electrical signals that are related to the analysis signals. The non-contact electroencephalography (EEG) device can also include a processor that is configured to analyze the analysis signal to detect patterns in the analysis signal corresponding to a state of the person in proximity to the non-contacting sensor.

In further aspects of the disclosure, the non-contact electroencephalography (EEG) device, can detect a state of the person in proximity to the non-contacting sensor that includes at least one of an emotional state, a cognitive load state, and an alertness state of the person in proximity to the non-contacting sensor. Further, when the processor detects a pattern corresponding to a predetermined state of the person in proximity to the non-contacting sensor, the processor can transmit an action signal to another device to take a subsequent action.

The non-contact electroencephalography (EEG) device according to the disclosure can include a processor that is configured to analyze the analysis signal to detect patterns in the analysis signal corresponding to an activity of the person in proximity to the non-contacting sensor. The activity of the person in proximity to the non-contacting sensor may include the moving of a head of a person in an affirmative gesture or a negative gesture. Further, the activity of the person in proximity to the non-contacting sensor can include the moving a head or a body of a person in into or out of proximity to the non-contact sensor, so that the non-contact electroencephalography (EEG) device detects whether a space monitored by the non-contact sensor is occupied or unoccupied, respectively, by the person. Additionally, when the processor detects a pattern corresponding to an activity of the person in proximity to the non-contacting sensor, the processor can transmit an action signal to another device to take a subsequent action.

Aspect of the disclosure can also include a non-contact electroencephalography (EEG) device where the non-contact sensor is integrated into at least one of a headrest, seat, stantion, and visor. Further, the non-contact sensor can be located remotely from a head of the person and adjacent to at least one of a neck, back, and gluteus of the person. The non-contact sensor can be configured in a bar array configuration or a concentric ring array configuration.

Additional aspects of the disclosure can provide a non-contact electroencephalography (EEG) device where the amplifying device can further include a high pass filter that is coupled to the non-contact sensor and that is configured to generate a first filtered signal by attenuating low frequency components of the detected electrical signals. The amplifying device may also include a first amplifier that is coupled to the high pass filter and that is configured to generate a first amplified signal by amplifying components of the first filtered signal that are related to the analysis signals. The amplifying device can further include a second amplifier that is coupled to the first amplifier and that is configured to generate a second amplified signal by amplifying components of the first filtered signal that are related to the analysis signals. The amplifying device may also include a low-pass filter that is coupled to the second amplifier and that is configured to generate a second filtered signal by attenuating high frequency components of the second amplified signal. In further embodiments, the amplifying device can include a third amplifier that is coupled to the low-pass filter and that is configured to generate the analysis signal by amplifying components of the second filtered signal that are related to the analysis signals.

BRIEF DESCRIPTION OF THE DRAWINGS

Various embodiments of this disclosure that are proposed as examples will be described in detail with reference to the following figures, wherein like numerals reference like elements, and wherein.

DETAILED DESCRIPTION OF EMBODIMENTS

Figure 1:
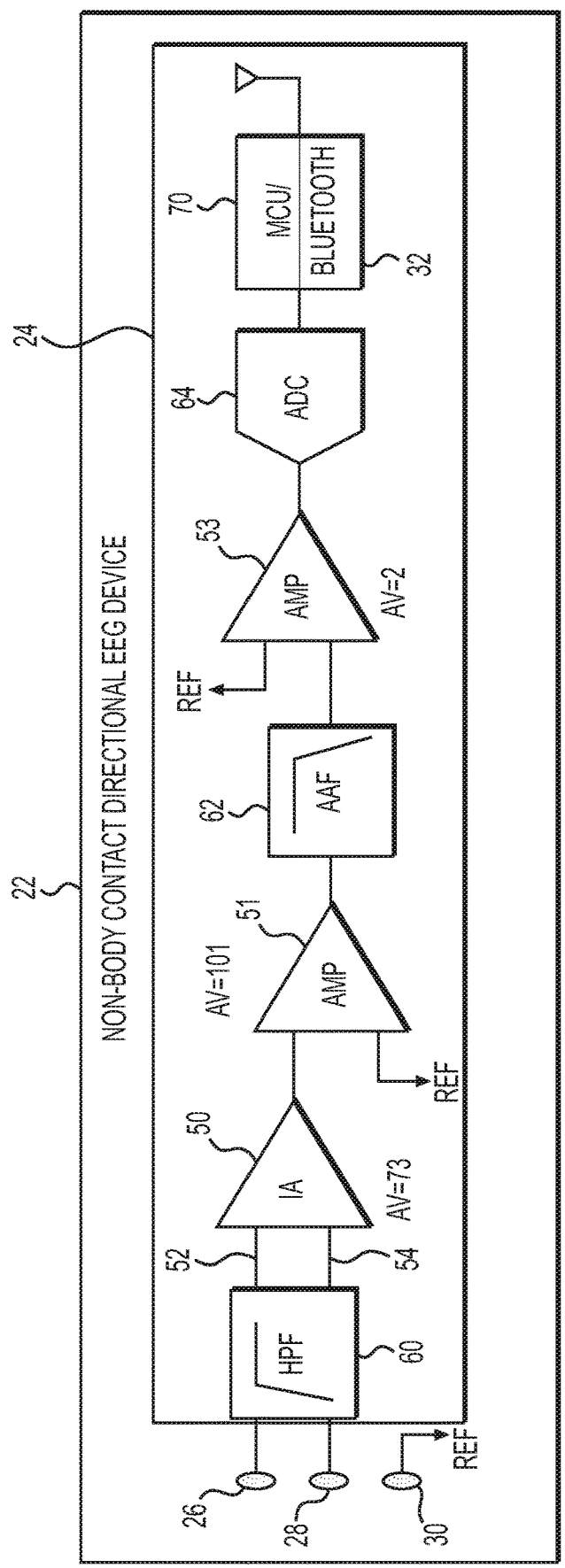
FIG. 1 is a schematic representation of a non-body contact directional EEG device according to an exemplary embodiment of the disclosure.

The apparatus and methods described in this disclosure can monitor brainwave activity of an individual without electrode attachment to the head or body of the individual. As described by this disclosure, non-contacting sensors can be placed proximate to portions of the head or body without touching either the skin of the head or body. For example, the non-contacting sensors may be used at a distance of six or more inches away from the body and obtain an EEG signal through various materials, such hair, clothing, upholstery, and the like. Additionally, the apparatus and methods for monitoring brainwaves described by this disclosure do not require signal injection into a subject. Further, the apparatus and methods for monitoring brainwaves described by this disclosure can be used anywhere on the body to acquire EEG signal in a manner similar to the famed 'Tricorder' of the Star Trek television series.

In embodiments, the apparatus may be integrated into a single device or multiple devices where sensors can be wired or wireless coupled to electronic circuitry that typically includes a processor that is configured to perform signal processing and analysis functions. In such an embodiment, a body-directional mount including sensors can be directed toward the head or body of an individual and be in communication with a separate processor that is configured to perform analysis, such as signal processing. Alternative embodiments can employ a single self-contained unit directed to the head or body that performs all data collection, signal processing, and analysis functions. Another embodiment employs a body-directional mount that is directed toward the head in communication with a separate analysis computer. Yet another embodiment employs a single self-contained unit directed to the body below the head performing all data collection, signal processing, and analysis functions. As described herein, none of the embodiments make contact with the skin of the body or head of a person being monitored.

Studies of the brain have found that EEG signals include a number of components, including signals resulting from rhythmic activity that fall within a number of frequency bands. Generally accepted terminology for signals within these various frequency bands includes delta (up to 3 Hz), theta (4 Hz to 8 Hz), alpha (8 Hz to 12 Hz), beta (12 Hz to about 30 Hz), and gamma (approximately 26 Hz to 100 Hz). Although these different brainwave signals are produced simultaneously and in combination, the frequency band within which signals are dominant (strongest) at any point in time is an indication of the state of consciousness of a person, or of the physiological state of the person.

As examples, during sleep, the brain produces dominant slow delta waves with a frequency range up to 3 Hz. These tend to be the highest in amplitude and are the slowest waves. Theta waves in the frequency range from 4 Hz to 8

Hz are commonly associated with daydreaming or being in the twilight of sleep or drowsiness. Alpha waves in the frequency range from 8 Hz to 12 Hz are indicative of relaxation. Beta waves in the frequency range from 12 Hz to about 30 Hz are associated with active thinking or alertness. Gamma waves in the frequency range approximately 26 Hz to 100 Hz are theorized to represent cohesiveness of different populations of neurons working together to form a network for the purpose of carrying out a certain cognitive or motor function. Because of filtering properties of the skull and scalp, gamma waves can are generally recorded by using electrodes placed directly on the exposed surface of the brain through an invasive procedure known as electrocorticography (ECoG) which requires a craniotomy.

Signal acquisition for monitoring electrical activity within the brain has been conventionally limited to the use of electrodes attached to the human head, and typically to the scalp, for a variety of reasons. Electrode placement on the head can be limiting for a variety of reasons. As one example, if a person is active in a sport or movement, electrical activity within the brain cannot be accurately monitored using head-bound EEG electrodes because the movement of the head during the activity interferes with the signal acquisition itself by creating artifacts. Moving electrodes can disrupt signal input/output. Also, if a person has a head injury or traumatic brain injury (TBI), that person may not be able to withstand sensors placed on the head due to tissue damage. For use in a vehicle, attachment of electrodes to the head has been rejected by the public. Contact or even close proximity to the skin of the head incorporated in traditional wired EEG acquisition sensors and modern consumer headsets have made EEG use somewhat prohibitive in the consumer marketplace. For example, they can reinforce a negative science fiction stereotype that connotes an intimidating or frightening effect attributable to visible wires attached to the head.

The apparatus disclosed herein can be particularly useful in the fields of monitoring EEG-based biofeedback, detecting cognitive state, detecting human emotions, detecting cognitive load, and detecting drowsiness and sleep. However, such are by way of example only, and not limitations. Accordingly, embodiments of the disclosure may be employed to acquire and analyze signals based on electrical activity within the brain of a person for a wide variety of purposes.

For example, the apparatus can be used in vehicles, such an automobile or airplane, to detect attention/distraction of a vehicle operator. Additionally, the apparatus can be used to measure cognitive load of a vehicle operator, such as the balance between short-term memory which briefly stores information and working memory which minimally processes information before it gets placed in long-term memory. A vehicle operator's performance can be impaired with too great a cognitive load, i.e., too much information to process. This can include the operator's ability to detect safety-critical events. Contributors to cognitive overload are often engineered into modern vehicles and can include infotainment systems, navigation systems, telecommunications, and the like. These devices can be deadly when coupled with distraction caused by moving one's eyes from the road to interact with such devices.

The apparatus can also be used in vehicles to detect operator drowsiness. Conventional eye detection or ocular techniques monitor eye droop and eye blinks to detect drowsiness. Detection by these techniques can often occur too late, as the driver is very close to full sleep by the time drowsiness is actually detected. The apparatus described in this disclosure has the potential to detect drowsiness far sooner than the conventional ocular technology.

Further, the apparatus can be used to control devices. For example, based on a detected brain activity, the apparatus can be used to change the music that is played in a vehicle based on the driver's emotional state, change the air temperature by monitoring the driver's stress level, or even simplify the digital displays should the driver's cognitive load become too great.

In an embodiment, the apparatus may be incorporated into anything that comes into proximity with a person to be monitored, such as a headrest of a seat. The apparatus is able to perform non-contact monitoring of an individual that is a distance away from the apparatus, for example, 10 inches away. Further, materials, such as turbans, hats, hair, and the like, have little effect on signal detection. When incorporated into a headrest, relevant portions of the headrest can be selected from a material that causes minimum electromagnetic interference (EMI).

In yet other embodiments, the apparatus can be used to measure brainwave activity that are indicative of any activity. Once an activity is sensed, the apparatus can trigger further action. For example, the apparatus can be placed in headrests to monitor the responses to an audience viewing a new product, such as during a product 'pitch.' The apparatus can also be placed in headrests in casinos with video gambling, for example, so that the apparatus can detect disinterest, allowing the game to modify itself and keep the gambler in the chair longer. Additionally, the apparatus can be placed in mattresses where it can monitor the sleep of the sleeper (passive monitoring), and if the sleeper is experiencing insomnia, it can allow them to control an app on, for example, a tablet, PC, or phone, which will help induce sleep brain patterns, therefore allowing them to fall or remain asleep. Further, the apparatus can be placed in furniture (as well as some mattresses) where it can allow the recliner to fully recline if it senses that the user falls asleep. In a smart home or office environment, the apparatus can interact with smart devices. For example, if the apparatus detects that a person falls asleep, then the apparatus can signal other devices to turn off the lights, locks the doors, turn off the TV, and set a thermostat to a favorite sleeping temperature.

Specific examples of EEG-based biofeedback employed in attention training and in computerized training apparatus are disclosed in Freer U.S. Pat. No. 6,097,981 titled "Electroencephalograph Based Biofeedback System and Method;" in Freer U.S. Pat. Nos. 6,402,520 and 6,626,676 titled "Electroencephalograph Based Biofeedback System For Improving Learning Skills;" and in Freer U.S. Pat. Appl. Pub. No. 2004/0230549 titled "Systems and Methods for Behavioral Modification and Behavioral Task Training Integrated with Biofeedback and Cognitive Skills Training." Specific examples of EEG-based biofeedback employed in human performance training are disclosed in Freer U.S. patent application Ser. No. 12/112,528, filed Apr. 30, 2008, titled "Training Method and Apparatus Employing Brainwave Monitoring." All of the above are hereby incorporated herein by reference in their entirety into the present application.

Generally, single neurons are not measured by an EEG as the electrical field produced by ionization of neurotransmitters in the synaptic cleft can be too small to be detected. Instead, an EEG signal is the result of hundreds of thousands to millions of neurons firing. It is suspected that pyramidal neurons produce EEG signal as they are close to the surface of the cortex and are spatially aligned. Thus, EEG is a summation of at least hundreds of thousands to millions of neurons which produces a field of energy also termed volume conduction. The minute EEG signal produced by cells close to the surface of the cortex must travel through multiple media (cerebrospinal fluid, meninges, skull, and dermis) before reaching the surface of the dermis where the sensors detect it. Thus, it can be polluted, smeared, or otherwise distorted even under the best circumstances. Indeed, an EEG poorly measures neural activity that occurs below the upper layers of the brain (the cortex). Further, unlike a functional magnetic resonance imaging or functional MRI (fMRI) which can view active brain regions, an EEG requires protracted analysis to even suggest what areas are activated by a particular response.

An EEG then, is a field of energy that encompasses a wide area over the neurons that are producing the signal. Conventionally, these minute signals can be monitored by placing sensor plates directly over the field or millimeters from it, such as in a skull cap worn by a person. This method essentially forgoes the ability to look at the entire field, but instead focuses on the deliberate attempt to monitor specific, localized data points. For clinical use, this is highly functional as it's believed that certain local sites provide distinct information about the brain needed to diagnose and treat abnormalities, dysfunctions, or dysregulation. Typically, in a clinical EEG, the electronics consist of multiple stages with low gain on each stage. Each of the multiple stages, for example 6 to 10 amplifier stages, provides both amplification and a two pole filter to improve the signal-to-noise ratio. An example would be a 2-pole filter at six stages equaling a 12-pole filter.

Such conventional EEG acquisition, i.e., stacking amp-filter, amp-filter provides the best solution for clinical use in monitoring local field energy. However, contrary to the techniques described in the present disclosure, conventional EEG acquisition will not acquire EEG signal either from the body below the head, nor even from more than a few millimeters from the head before the signal is lost. This is due to the inherent signal loss and increased signal to noise ratio of the amp-filter, amp-filter stacking method found in conventional clinical EEG devices. In essence, using the amp-filter, amp-filter stacking method, one would simply be amplifying noise if one attempts to measure EEG away from the head. Thus, conventional clinical EEG devices are incapable of either distinguishing EEG signal from the body below the head, or sensing EEG from the head if their sensor plate is more than a millimeter or so away. This is also a reason that it was thought impossible to measure EEG from the body below the head or from significant distances away from the head.

FIG. 1 shows an exemplary block diagram of a non-body contact directional EEG device 22 according to an embodiment of the disclosure. As shown, the device 22 can include a high-pass filter 60 coupled to three amplifiers 50, 51, and 53. The high-pass filter 60 provides a first input 52 and a second input 54 to the amplifier 50. Further, an antialiasing filter 62 can be arranged between the two initial amplifiers 50, 51 and the final amplifier 53. The output of the final amplifier 53 is received by an analog-to-digital converter (ADC) 64 and subsequently transmitted to a controller/wireless transmitter 70. The above components are collective grouped into an amplifier and wireless transmitter unit 24 of the non-body contact directional EEG device 22.

The device 22 can further include non-contact sensors 26 and 28 that collect EEG data from a person and are coupled to the high pass filter (HPF) 60. Further, a ground or reference electrode 30 can be included as part of the sensor array. The non-contact sensors 26 and 28 can be AC coupled to the high pass filter 60 to reduce or prevent any possibility of DC current flowing into the human subject and preventing DC input offset in the amplifier from overdriving the subsequent stage. For example, HPF 60 can block DC offset that can occur in a space between electrodes and skin due to an electrochemical reaction. The cut-off frequency in this system can be set to 1 Hz, and thus any signal higher than 1 Hz will pass through the filter while any signals below 1 Hz will be attenuated by 60 dB/decade. Such method can greatly amplify all noise including 60 Hz.

In operation, and after passing through the high pass filter 60, a first filtered signal including the attenuated EEG raw signal from a person can be greatly amplified by the initial single stage amplifier 50 to generate a first amplified signal. The first amplification stage 50 can be, for example, a differential instrumentation amplifier with a gain of 73 that can be coupled to a second amplification stage, rather a filter as is done in conventional systems.

The second amplification stage 51 can receive the first amplified signal and can be a single-ended inverting amplifier with a gain of 101, for example, that can be AC coupled to the first stage 50. In operation, the second stage 51 can output a second amplified signal that can be transmitted to an 8th order elliptical low-pass filter, such as antialiasing filter 62, that can be implemented having a monolithic switched capacitor integrated circuit. The filter's −3 db or corner frequency can be set to 40 Hz which also happens to be the upper limit for beta frequency band. This frequency setting is below 75 Hz (sample rate=150 samples/second) allowing it to serve as an antialiasing filter 62, thus removing the largest interfering signal of 50/60 Hz AC line noise and components above the Nyquist frequency of 75 Hz, prior to ADC sampling.

In operation, the antialiasing filter 62 can be configured to attenuate or minimize signal frequency components which are above a frequency band of interest and which are unrelated to electrical activity within the brain of a person. A potential frequency component unrelated to and not relevant to brain electrical activity is a signal coupled from 50 Hz or 60 Hz AC power lines. As an example, a low pass filter having a cut-off frequency within the range 20 to 40 Hz can be suitable. In a more particular example, the low pass filter 62 is a fifth order switched capacitor low pass filter having a cut-off frequency of 22 Hz. In the FIG. 1 embodiment, brainwave signal components of interest are well below 50 Hz or 60 Hz, and a 22 Hz low pass filter can be simple and effective. In applications in which frequency ranges of brainwave signal components of interest include 50 Hz or 60 Hz, a notch filter may be employed instead of the low pass filter.

The antialiasing filter 62 outputs a second filtered signal that can then pass to a third amplification stage 53 that can be a single-ended inverting amplifier with a gain of 2, for example, that is AC coupled to the antialiasing filter 62. The third amplification stage 53 can transmit an analysis signal to the ADC 64. In an exemplary embodiment, the ADC 64 used can be 12 bit, and a 12 bit binary number can have a range from 0 to 2 to the 12th power minus 1, and therefore permits output from 0 to 4095. The ADC 64 (12 bits) can have a range: 2.7 Volts with a precision 670 microV. The total gain for the system can be 14,746 minus the attenuation of the filter stage. This provides detection of EEG signal down to 100 nanovolts (nV) at the sensor array's surface ("nano" represents a factor of $10^{-9}$, so 1 nanovolt=$10^{-9}$ volts).

This is a significant difference from conventional EEG acquisition technology that can only detect millivolts (mV;

a unit of potential difference equal to one thousandth or merely $10^{-3}$ of a volt). This can be a matter of convenience, as the use of sensors attached directly to the head or in very close proximity to the head require far less amplification in order to detect power spectrum band powers, that are reported in units such as Volts-squared per Hz ($V^2$/Hz). Millivolts are used due to the close proximity of the sensors to the energy they detect. This is necessary in clinical applications to view localized energy in specific areas of the brain.

The output of the ADC 64 can be a digital version of the analysis signal and can be coupled to a microcontroller 70 and a wireless transmitter, such as a Bluetooth® device 32. In operation, the microcontroller 70 can analyze the analysis signal to recognize patterns in the signal that correspond to particular brainwave activity. For example, the microcontroller 70 can identify patterns in the analysis signal corresponding to mental states of an individual, such as an emotional state, a cognitive load state, and an alertness state of a person being monitored. Additionally, the microcontroller 70 can identify patterns in the analysis signal corresponding to an activity of the person in proximity to the non-contacting sensor including, for example, when that person moves their head in an affirmative or a negative motion. Also, the microcontroller 70 can identify patterns in the analysis signal corresponding the activity of the person in proximity to the non-contacting sensor including when the person moves their head or body into or out or proximity to the non-contact sensor so that the non-contact electroencephalography (EEG) device detects whether a space monitored by the non-contact sensor is occupied or unoccupied.

Further, the microcontroller 70 can be configured to control the components of the amplifier and wireless transmitter unit 24 to process the detected EEG data and wirelessly transmit the EEG data to other devices, as necessary. Additionally, under the control of the microcontroller 70, detected EEG data can be transmitted to other devices for further processing and/or control of other devices.

The non-body contact directional EEG device 22 described in the present disclosure permits this system to obtain EEG signals from the body below the head without contact from the head or body from 10 inches or more away from an individual. The non-body contact directional EEG device 22 described in the present disclosure does not require close proximity or contact to the head or body below the head to acquire EEG signal. The significantly different technique requires the monitoring of all available field energy emanating from the brain in real-time. Compared to conventional systems, this can be considered as different as oil drilling is to gold mining. In other words, instead of attaching a sensor to gain localized information from the brain, the proposed system can continually pull in all available electrical field data of brain information for extensive processing to parse the data into usable EEG data.

Additionally, the non-body contact directional EEG device 22 described in the present disclosure is capable of converting the incredibly small amount of detected nanovolt energy into usable information. For example, the values attained can be converted using two digit base 64 numbers to base 10, and subtract 2048 to reconstitute the information into a signed waveform between −2048 and +2047. This is an AC waveform centered about 0. The useable information can then be passed through a digital filtering algorithm, a RMS (root mean square) algorithm, as well as other algorithms, such as those designed to translate brain wave information into attentiveness, anxiety level, drowsiness or another measure of brain state. Thus, as opposed to conventional systems, the values have undergone a number of complicated transforms and rescale operations from the original voltage measurements, there is no longer a simple linear correlation to units of Volts.

Another distinguishing feature of the non-body contact directional EEG device 22 is the use of non-contact sensor arrays to acquire EEG field energy emanating from volume conduction. Conventional systems utilize single sensors for localized acquisition of an EEG signal. These sensors must be very close to the head or directly attached to the head to acquire signal. As described in the present disclosure, non-contact arrays can be used as a single channel electric field detection system. This method can provide distinct advantages over other systems, as the sensor array can detect not only brain signal from up to 10 inches or more, but can also detect a position of a head. For example, if mounted in a headrest, the array can detect whether the seat occupant is looking left, right, down, or up.

Additionally, the use of an array can also permit detection of motion of the occupant's head. As a non-limiting example, if an person's head were to shake left to right in the universal sign for 'No,' the motion creates a distinctive wave pattern as the head moves across the array from left to right or right to left. Additionally, if the occupant nods their head to indicate 'yes' that motion produces a distinct pattern of its own. So, in a vehicle, the commands, 'yes', and 'no', are recognizable without the driver's hands ever leaving the wheel or eyes leaving the road.

Another use for the non-body contact directional EEG device 22 described in the present disclosure can involve using the arrays as a screening device at an airport or hotel. For example, if the arrays can be placed in stanchions in an entryway, the apparatus can be used to measure anxiety, stress, and/or temperament of individuals who pass through. Similarly, if used in a headrest or seatback, the arrays could alert flight crews to the temperament of a seat occupant or alertness of a pilot. Further, the arrays can be uses to simply determine whether a seat is occupied or unoccupied which can be useful in automated driving situations.

In FIG. 1, the non-contact sensors 26 and 28 can be any type of non-contacting electrode, such as "dry" electrodes which do not require a conductive gel or paste and that are not in physical contact with the body, as well as non-contact or contactless biopotential sensors. As active sensors, the sensors 26 and 28 may be configured in various arrays or having different size and shape of electrodes. For example, multiple sensors can be designed in various patterns and sizes, such as a concentric ring or parallel bar pattern, depending on design considerations, as well as their intended use.

In operation, the sensor array can collect EEG data, as well as provide directionality of the received signal. In other words, the non-contact sensor array 26 and 28 can be aimed to receive signal from various portions of either the head or body. This establishes a unique application of the technology in that it can collect an abundance of EEG data from a single array. The addition of more sensor arrays by adding channel capacity can increase the amount of information to be collected. This is analogous to an array of radio telescopes looking into the vastness of the universe that work together as a single telescope to provide higher resolution by means of interferometry. The advantage of this technique in the current system is that it can produce EEG data in the abundance of a clinical EEG skullcap without using a skullcap which is tedious, invasive, and inappropriate for consumer use. Additionally, the use of multiple non-contact hidden arrays, for example five to six, can minimize the need for many sensors, often 30 to 60 plus in a clinical skullcap. Secondly, the configuration of such arrays not only increases signal fidelity and data quantity, it can also be utilized to ascertain a direction in which the human head is looking, as signal strength detecting within each array varies with the position of the head. In a moving vehicle, for example, this information is imperative regarding where the driver is paying attention. Looking away from the road ahead out a side window or to the engineered distraction of a display console can produce disastrous results.

The non-body contact directional EEG device 22 can be configured for placement near a portion of a person's head or body. Various specific embodiments thereof are described in detail herein below with reference to FIGS. 4-12. Thus, during use, the non-contact sensors 26 and 28 are placed at least proximate to portions anywhere on the body of a person. The non-contact sensors 26 and 28 develop raw signals including frequency components relevant to brain electrical activity ("brainwave" signals). This is essentially a brute force method of signal collection because the initial signal may be: a) quite far from the source (brain), possibly a distance from the head or collected from the body perhaps, e.g., the shoulder or low back, and is significantly smaller than the signal from a head-based clinical unit; b) obtained through material, such as light cloth or hair, from a distance of six to ten inches; c) obtained from a distance of six to ten inches from the skin of the body.

As a signal diminishes with the square of the distance, the signal at the body, away from the head, can be in nanovolts. In examples, the minute signal that is collected in the high pass filter 60 should then be greatly amplified in a single stage amplifier 50 with an average gain of 73. This differential instrumentation amplifier 50 is AC coupled to an operational amplifier 51 or 'op-amp' with an average gain of 101. The anti-aliasing filter 62 can then be applied that is an 8th order low pass filter implemented with a monolithic switched capacitor device. The −3 db frequency for this function is 40 Hz which also happens to be the upper limit for beta frequency band. The anti-aliasing filter can eliminate components above the Nyquist frequency of 75 Hz prior to ADC sampling. The antialiasing filter 62 can then be coupled with the final amp 53 with an average gain of 2. This unique combination produces an extraordinarily powerful EEG detector down to 100 nanovolts, and thus provides the ability to detect data heretofore undetectable from distances exceeding 6 inches from the head, or through the body away from the head without contact.

The various elements within the amplifier and wireless transmitter unit 24 of FIG. 1 may be implemented employing a combination of digital and analog technologies. Moreover, the amplifier and wireless transmitter unit 24 may be implemented as an "intelligent" and reprogrammable device, with the microcontroller 70 executing software to perform various functions. The microcontroller 70 is capable of wireless bidirectional data communications, facilitating modifications and adjustments of the functioning of the amplifier and wireless transmitter unit, such as by updating "firmware."

It will be appreciated that while shown as a single device, the functions of the device can be accomplished in various ways through the use of a single device, such as the amplifier and wireless transmitter unit 24 shown in FIG. 1, or alternatively distributed across multiple devices. For example, the brainwave signals can be collected by a first device and transmitted to a second device for processing.

Figure 2:
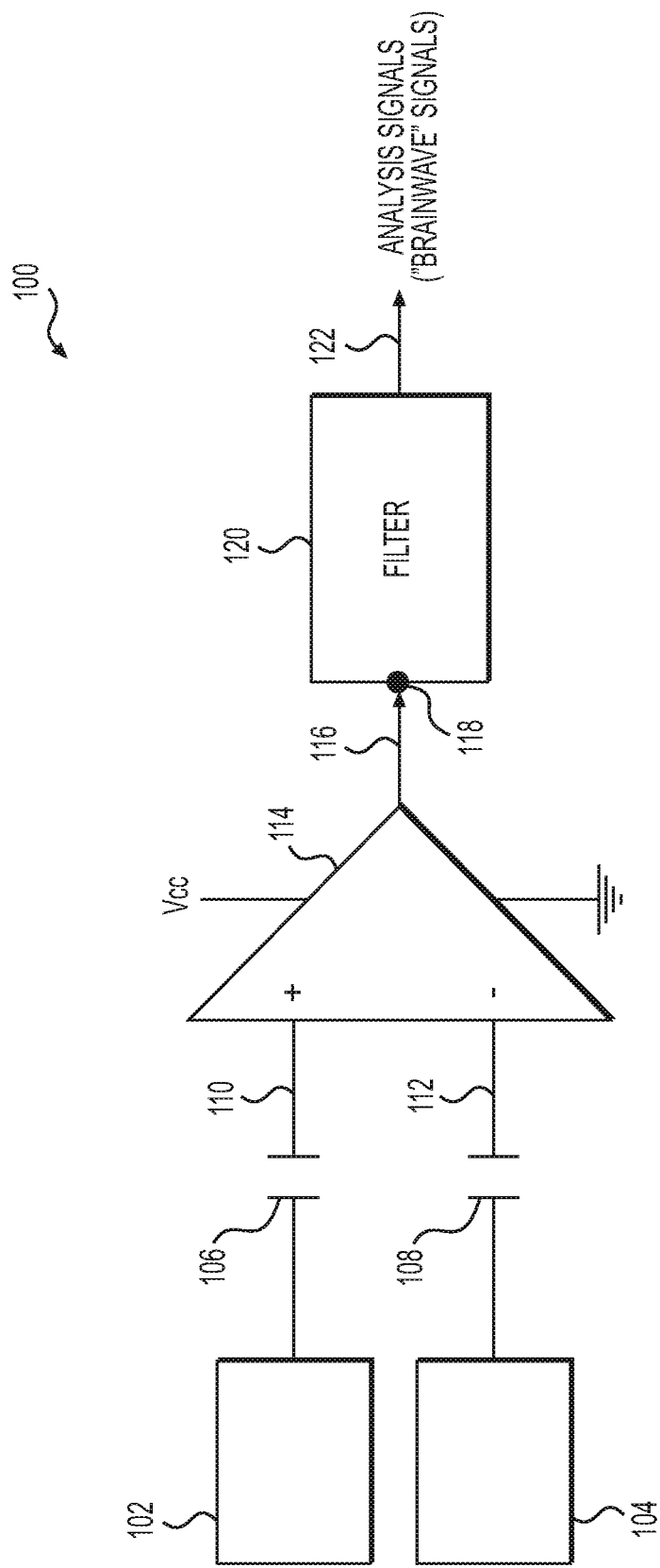
FIG. 2 is a schematic representation of a non-body contact directional EEG device according to an exemplary embodiment of the disclosure.

FIG. 2 show an exemplary embodiment of a generalized apparatus 100 which produces analysis signals including frequency components relevant to brain electrical activity. The FIG. 2, apparatus 100 can include two representative non-contact sensors 102 and 104, such as active electrodes, that can be coupled through capacitors 106 and 108 to high impedance inputs 110 and 112 of an amplifier 114. The non-contact sensors 102 and 104 can be positioned proximate to portions of a person's body to detect raw brainwave signals. The amplifier 114 has an output 116 connected to an input 118 of a filter 120. The signal processing in FIG. 2 can be analog, digital, or any combination thereof.

The filter 120 attenuates frequency components which are unrelated to frequency components of interest and which are not relevant to brain electrical activity. Produced at an output 122 of the filter 120 are what may be termed analysis signals corresponding to brainwave signals for further processing and analysis, the analysis signals including frequency components relevant to brain electrical activity. As described hereinabove with reference to the filter 62 of FIG. 1, the FIG. 2 filter 120 can be a low pass filter or a notch filter, as examples. The selection and design of the filter 120 depend on the frequency components of interest relevant to brain electrical activity, as well as on particular unrelated frequency components which are anticipated. The filter 120 may be implemented employing digital signal processing (DSP) techniques, and may be adaptive.

The "brainwave" signals at the output 122 of the low pass filter 120 may be employed for a variety of purposes. As described hereinabove, the signals at the output 122 are analysis signals which include frequency components relevant to brain electrical activity, with unrelated frequency components attenuated. The non-contact sensors 102 and 104 are positioned at least proximate to portions of the body of a person below the head to develop raw signals.

When frequency components relevant to brain electrical activity in general are of interest, particularly when frequency components including delta waves (up to 3 Hz) are of interest, signal components corresponding to a person's heartbeat (approximately 1 Hz to 2 Hz) are unrelated frequency components of particular concern. Unrelated frequency components corresponding to electrical activity of a person's heart are particularly high in magnitude when sensors are connected to portions of the body below the head. The apparatus described herein may be embodied in systems in which signal components in the raw signals resulting from electrical activity of a person's heart are actively attenuated. In an ideal case, signal components resulting from electrical activity of a person's heart are entirely cancelled by active cancellation.

Figure 3:
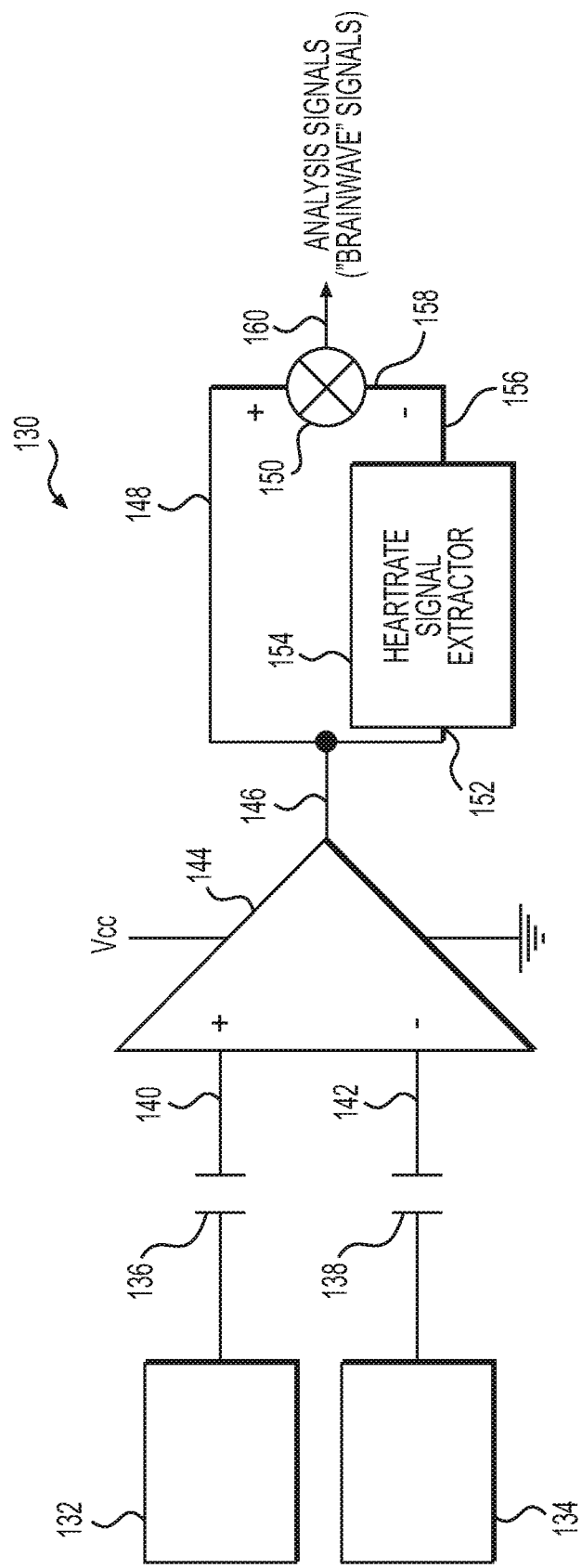
FIG. 3 is a schematic representation of a non-body contact directional EEG device according to an exemplary embodiment of the disclosure.

FIG. 3 is a representation of a generalized apparatus 130 which employs such active attenuation to produce analysis signals including frequency components relevant to brain electrical activity. The FIG. 3 apparatus 130 again employs two representative non-contact sensors 132 and 134 connected through capacitors 136 and 138 to high impedance inputs 140 and 142 of an amplifier 144. At least the non-contact sensors 132 and 134 are positioned proximate to portions of the body of a person below the head to develop raw signals.

The FIG. 3 amplifier 144 has an output 146 connected to two signal branches. One branch is connected to a (+) input 148 of a summing junction 150, and the other to an input 152 of a heart rate signal extractor 154 which extracts signal components resulting from electrical activity of a person's heart. An output 156 of the heart rate signal extractor 154 is connected to a (−) input 158 of the summing junction 150. Analysis signals which include frequency components relevant to brain electrical activity with unrelated frequency components attenuated are produced at the output 160 of the summing junction 150.

Thus, within the summing junction 150, signal components resulting from electrical activity of a person's heart are actively attenuated. Again, in an ideal case, signal components resulting from electrical activity of a person's heart are entirely cancelled by active cancellation.

The heart rate signal extractor 154 can employ digital signal processing (DSP) techniques to recognize, isolate and track signal components resulting from electrical activity of a person's heart. Heart rate monitors can recognize and track a person's heartbeat or heart rate, typically presenting a digital display. The thus-recognized, isolated and tracked signal is provided as an output of the heart rate signal extractor 154. With appropriate magnitude adjustment, the frequency or signal components resulting from electrical activity of a person's heart can be attenuated or cancelled. Accordingly, the brainwave signal that does not include the electrical activity of a person's heart can be produced at the output 160 of the summing junction 150

Again, the brainwave signals at the output 160 of the summing junction 150 may be employed for a variety of purposes. The signals at the output 160 are analysis signals, which include frequency components relevant to brain electrical activity, with unrelated frequency components attenuated. Again, what is significant is that at least the sensors 132 and 134 are positioned proximate to portions of the body of a person below the head to develop raw signals.

As an alternative to the heart rate signal extractor 154 and summing junction of FIG. 3, the topology of FIG. 2 may be employed to provide similar functionality. More particularly, the FIG. 2 filter 120 may be an adaptive DSP filter programmed to attenuate signal components resulting from electrical activity of a person's heart, as well as other signals (such as coupled 50 Hz or 60 Hz AC power line signals) unrelated and not relevant to brain electrical activity.

Signal components resulting from electrical activity of a person's heart can be used for at least two other purposes in embodiments of this disclosure. One such other purpose is to ensure that a body directional device and, in particular, non-contact sensors 26 and 28, 102 and 104, or 132 and 134 are in fact directed at, but not in contact with, or otherwise functionally proximate the body of a person, for convenience collectively referred to as "presence." Ensuring such presence can be employed to ensure that sensed signal components within a brainwave frequency band are in fact representative of brainwaves and are not the result of stray signals coupled from environmental sources, in other words to validate that an EEG signal is being collected. Ensuring such presence can also be employed to conserve battery life, by entering a low-power "standby" mode when the absence of signal components resulting from electrical activity of a person's heart indicates no presence.

Another such other purpose is to combine indications resulting from brain electrical activity (i.e., EEG) and from electrical activity of a person's heart (i.e., EKG) for a more comprehensive analysis and indication of a person's cognitive and physiological state. Embodiments of this disclosure thus provide the foundation for a dual technology approach (EEG and EKG) for more comprehensive physiological state monitoring.

FIGS. 4-12 illustrate examples of using a non-body contact directional EEG device with a person, according to the various embodiments of the disclosure.

Figure 4:
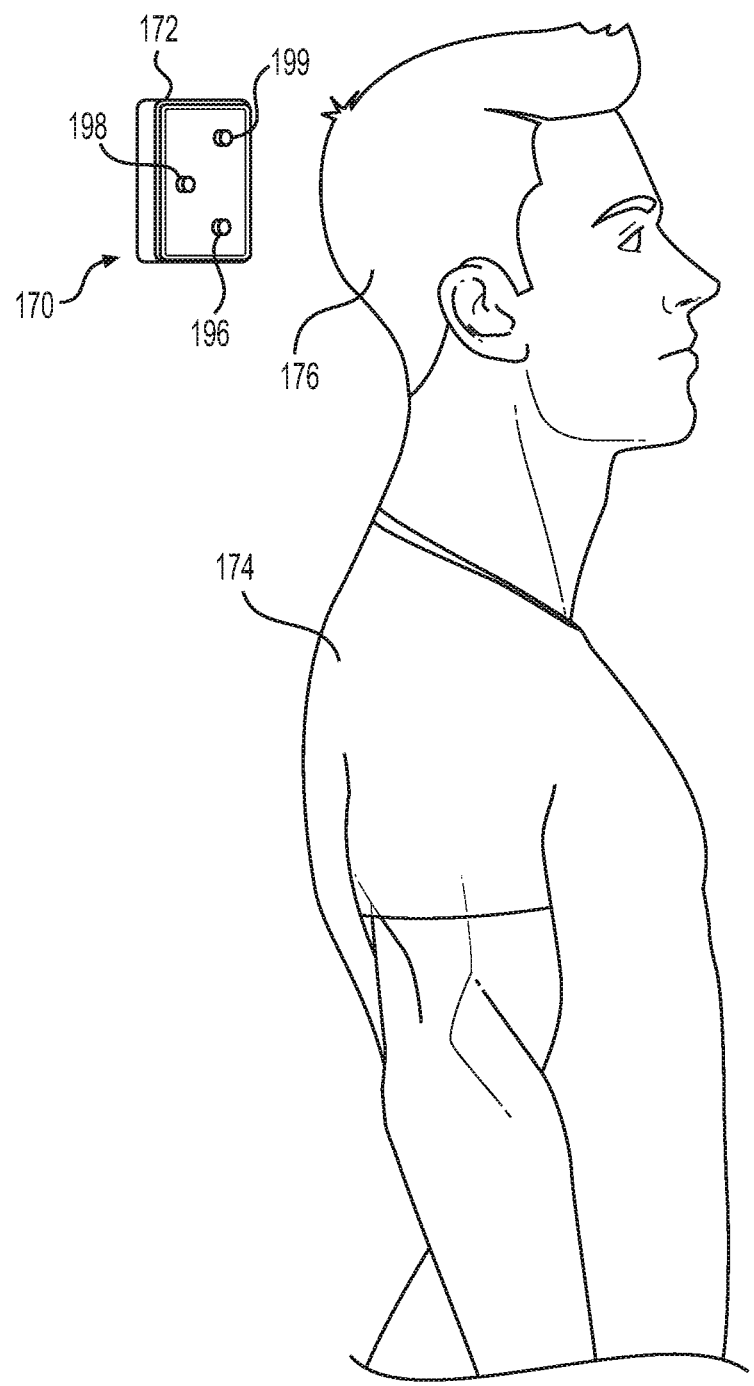
FIG. 4 illustrates a non-body contact directional EEG device according to an exemplary embodiment of the disclosure directed to a back of a head of a person.
Figure 5:
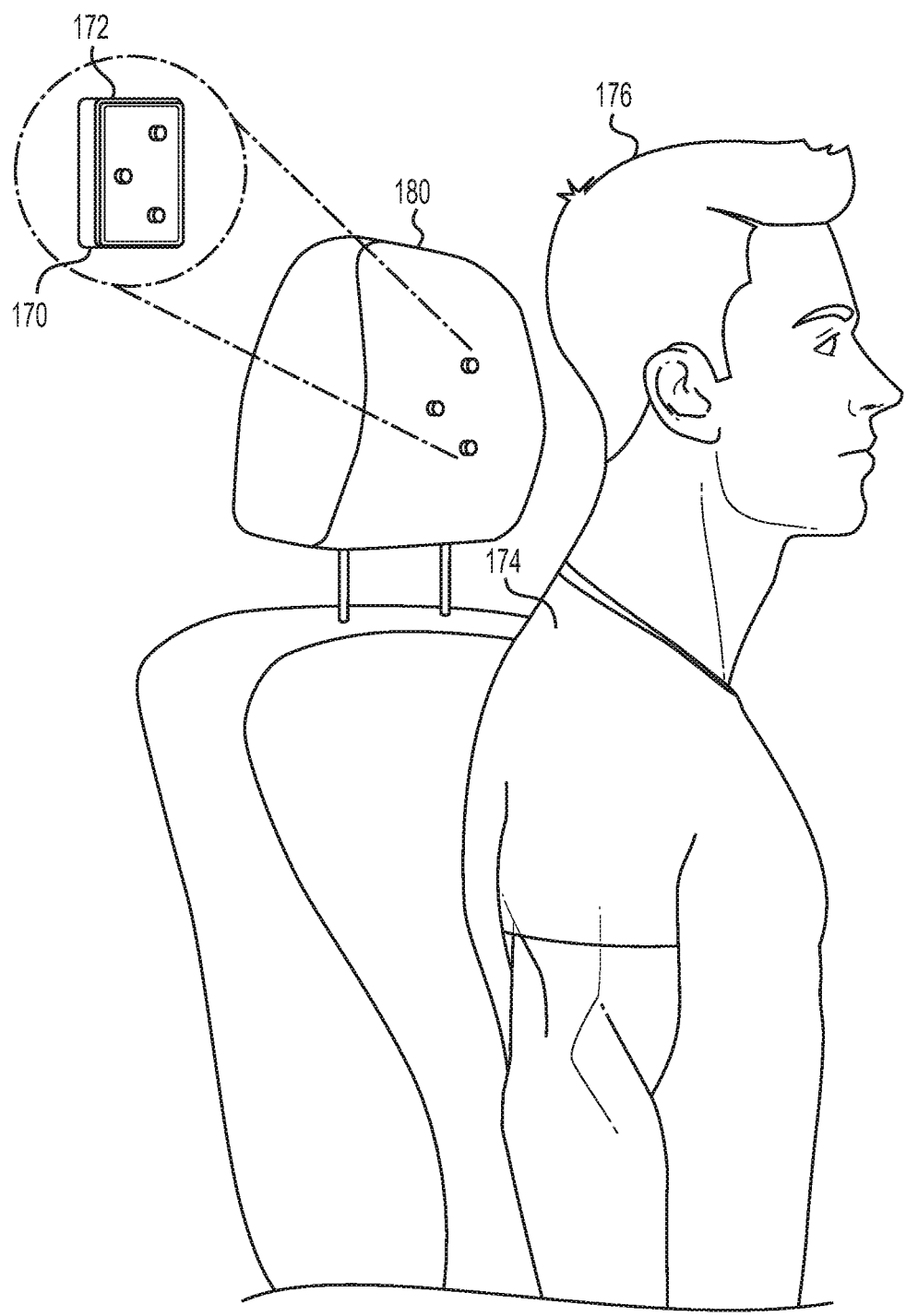
FIG. 5 illustrates a non-body contact directional EEG device according to an exemplary embodiment of the disclosure directed to the back of the head of a person from a headrest.

The non-body contact directional EEG device 170 or at least the non-contact sensors 198 and 199 of FIGS. 4-5 is configured for directional aiming to a portion of the head of a person 174. The non-body contact directional EEG device 170 can include at least non-contact sensors 198 and 199, reference electrode 196, as well as the amplifier and wireless transmitter unit 172, and more particularly takes the form of a housing configured for directional aiming of the device to the head 176 (FIG. 4). As shown in FIG. 5, the non-contact sensors 198 and 199 can be integrated into a headrest 180 portion (FIG. 5) of a seat in which the person 174 is sitting and detect the brainwave activity of the person 174.

Figure 6:
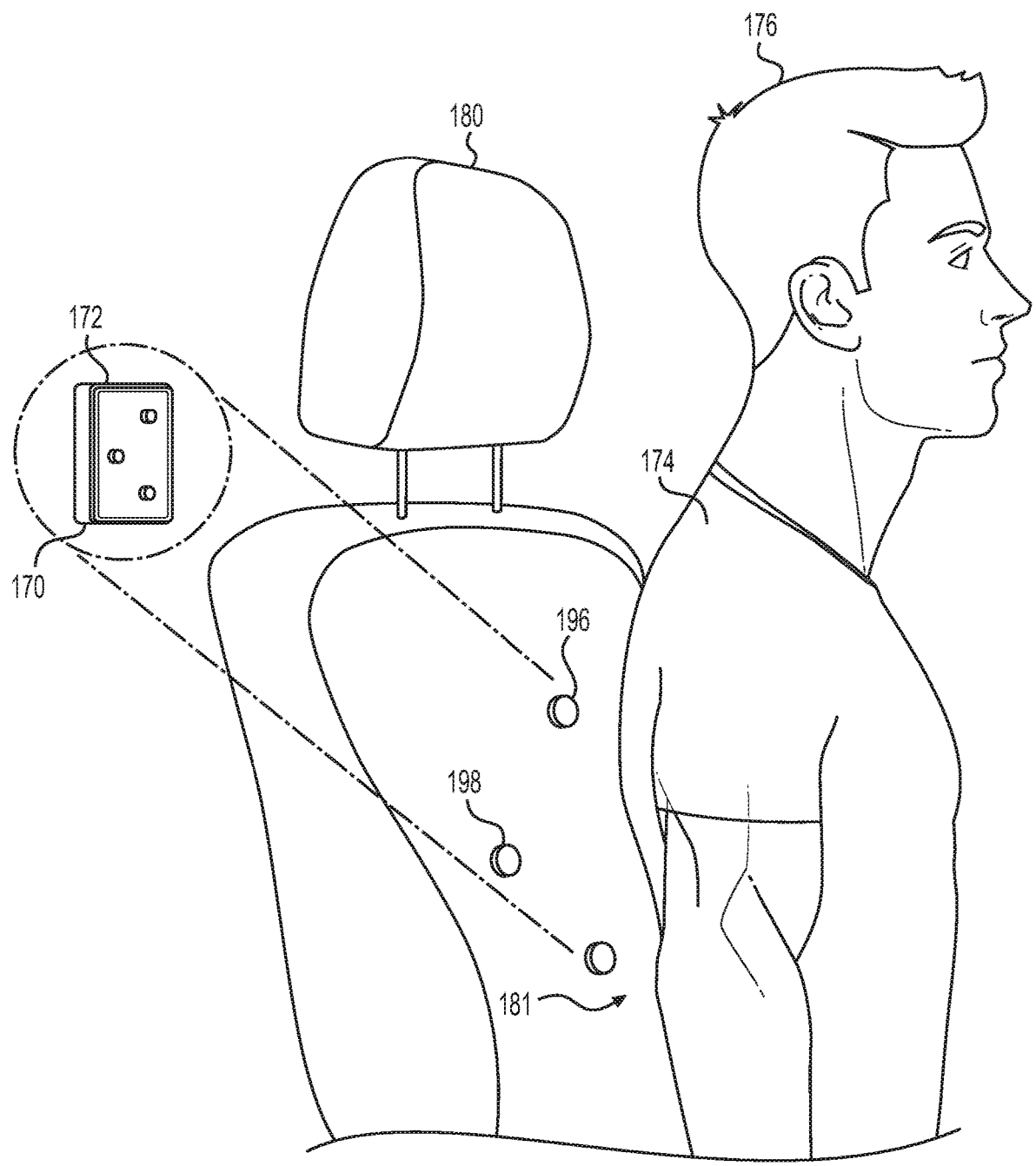
FIG. 6 illustrates a non-body contact directional EEG device according to an exemplary embodiment of the disclosure directed to a back of a person from a seatback.
Figure 7:
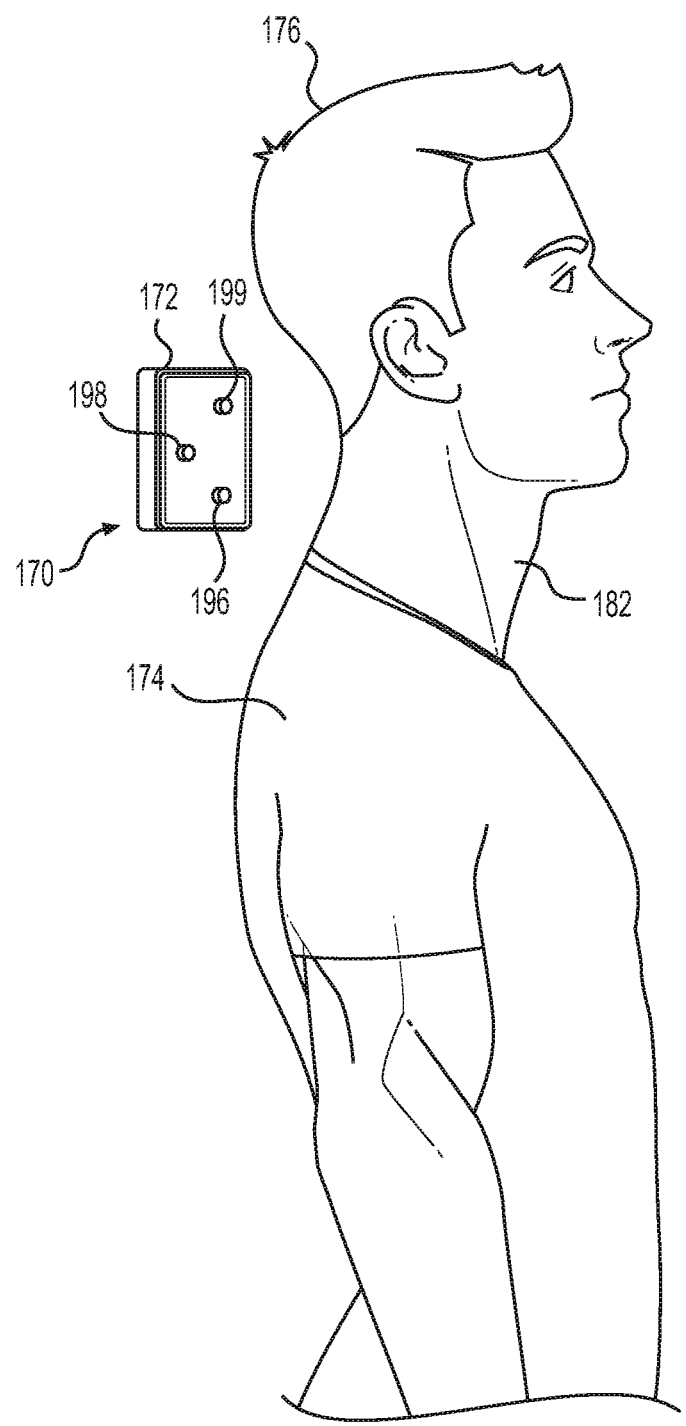
FIG. 7 illustrates a non-body contact directional EEG device according to an exemplary embodiment of the disclosure directed to the back of a neck of a person without touching the skin of the person.

In FIGS. 6-7, the non-body contact directional EEG device 172 or at least the non-contact sensors 198 and 199 can be configured for directional aiming to a portion of a back 181 of the person 174. Again, the non-body contact directional EEG device 170 can include at least non-contact sensors 198 and 199, as well as the amplifier and wireless transmitter unit 172, and more particularly takes the form of a housing 170 configured for directional aiming of the device to the back 181 (FIG. 6) or the back of the neck 182 (FIG. 7) of the person 174. As shown in FIG. 6, the non-contact sensors 198 and 199 can be integrated into a seat in which the person 174 is sitting and detect the brainwave activity of the person 174.

Coupled to and/or supported by the housing 170 are a pair of non-contact sensors 198 and 199 corresponding to the sensors 26 and 28 described hereinabove with reference to FIG. 1 that may also include a ground electrode 196 corresponding to the ground electrode 30 in FIG. 1. The sensors 198 and 199 can be electrically connected to the amplifier and wireless transmitter unit 172 and operate as described hereinabove with reference to FIG. 1. The sensors 198 and 199 thus, during use, are placed at least proximate to a portion of the person's 174 head (FIG. 5) or the back of the body 182 (FIG. 6).

Figure 8:
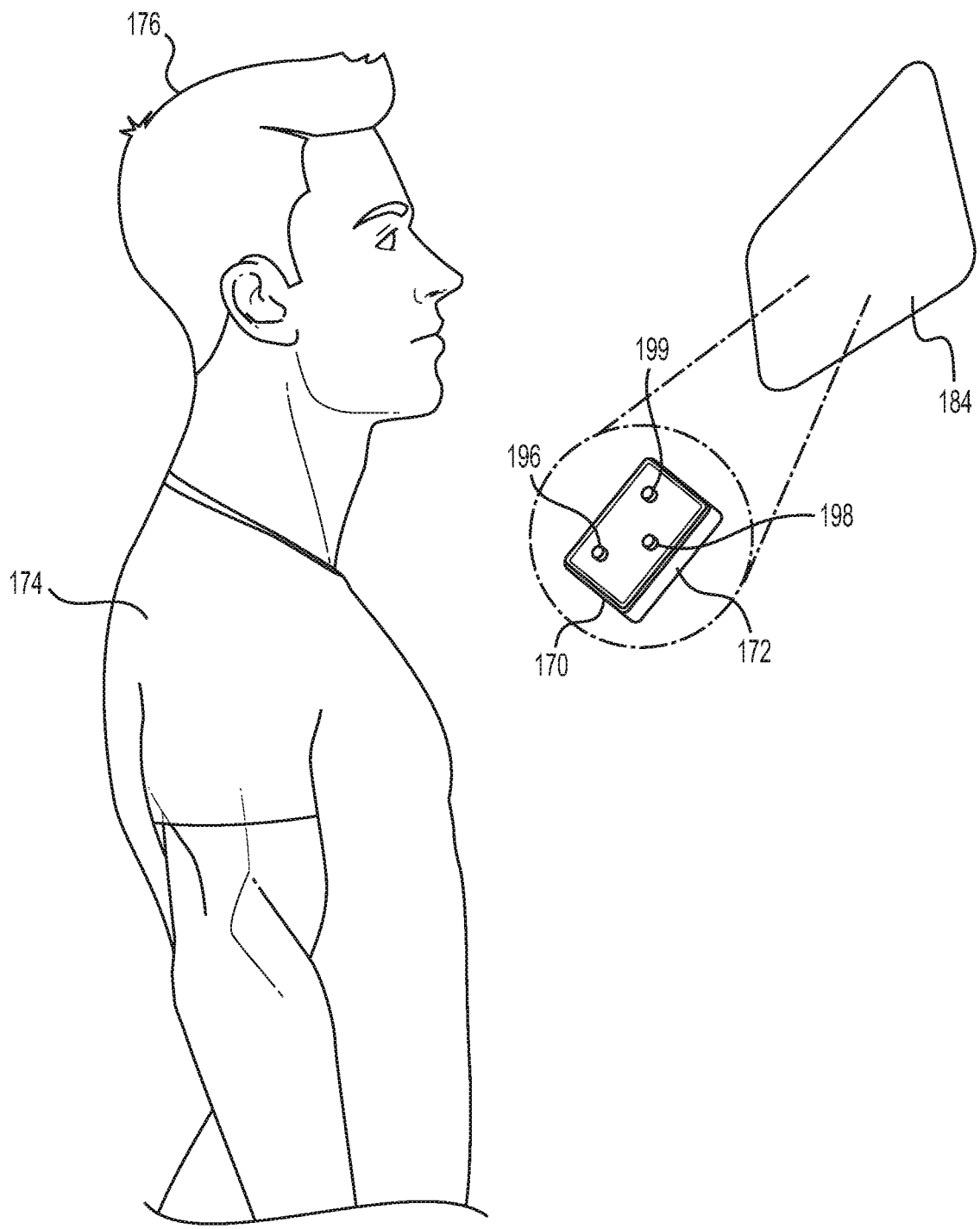
FIG. 8 illustrates a non-body contact directional EEG device according to an exemplary embodiment of the disclosure directed from an automobile visor to a forehead of a person without touching the skin of the person.
Figure 9:
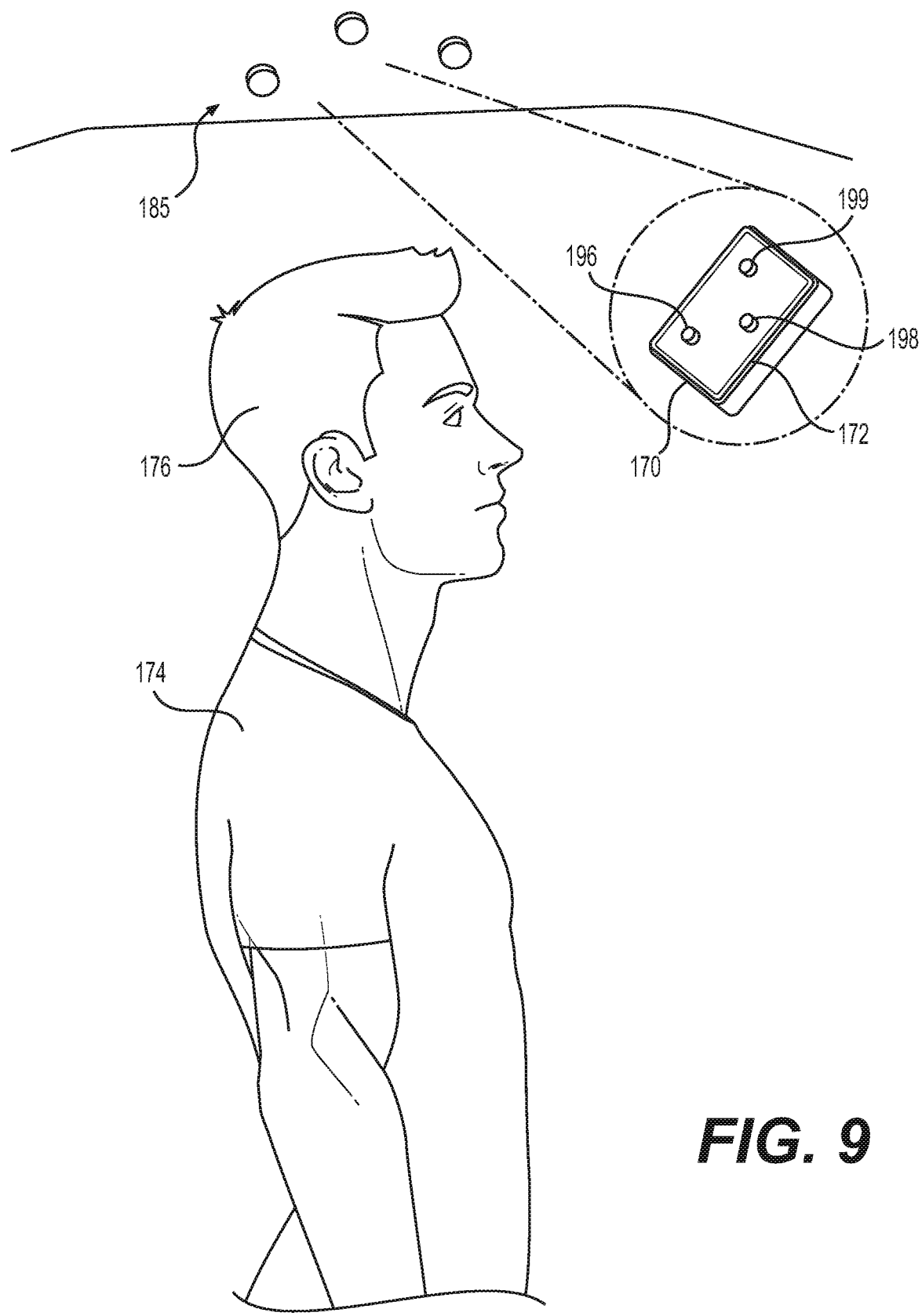
FIG. 9 illustrates a non-body contact directional EEG device according to an exemplary embodiment of the disclosure directed to a top of the head of a person without touching the skin of the person from an automobile ceiling.

In FIGS. 8 and 9, the non-body contact directional EEG device can be configured for placement adjacent to a portion of the head 176 of a person 174. The non-body contact directional EEG device 170 provides structural support for the amplifier and wireless transmitter unit 172, and the non-contact sensors 196 and 198 can be integrated into an automobile sun visor 184 configured for direction at the head 176 of the person 174.

In FIG. 9, describes an embodiment where the non-body contact directional EEG device or at least the non-contact sensors 198 and 199 can be configured for placement in proximity to the head 176 of the person 174. The non-body contact directional EEG device 170 including the amplifier and wireless transmitter unit 172, as well as non-contact sensors 198 and 199 can be integrated into, for example, an automobile interior ceiling 185 configured for direction towards the head 176 of the person 174.

Also supported by the visor and ceiling placement of FIGS. 8-9 are a pair of active non-contact sensors 198 and 199 corresponding to the non-contact sensors 26 and 28 described hereinabove with reference to FIG. 1, that may include a ground electrode 196 corresponding to the ground electrode 30 in FIG. 1. The non-contact sensors 198 and 199 are electrically connected to the amplifier and wireless transmitter unit 172, and operate as described hereinabove with reference to FIG. 1. The non-contact sensors 198 and 199 thus, during use, are placed at least proximate to a portion of the person's 174 body near the head 176 and detect the brainwave activity of the person 174.

Figure 10:
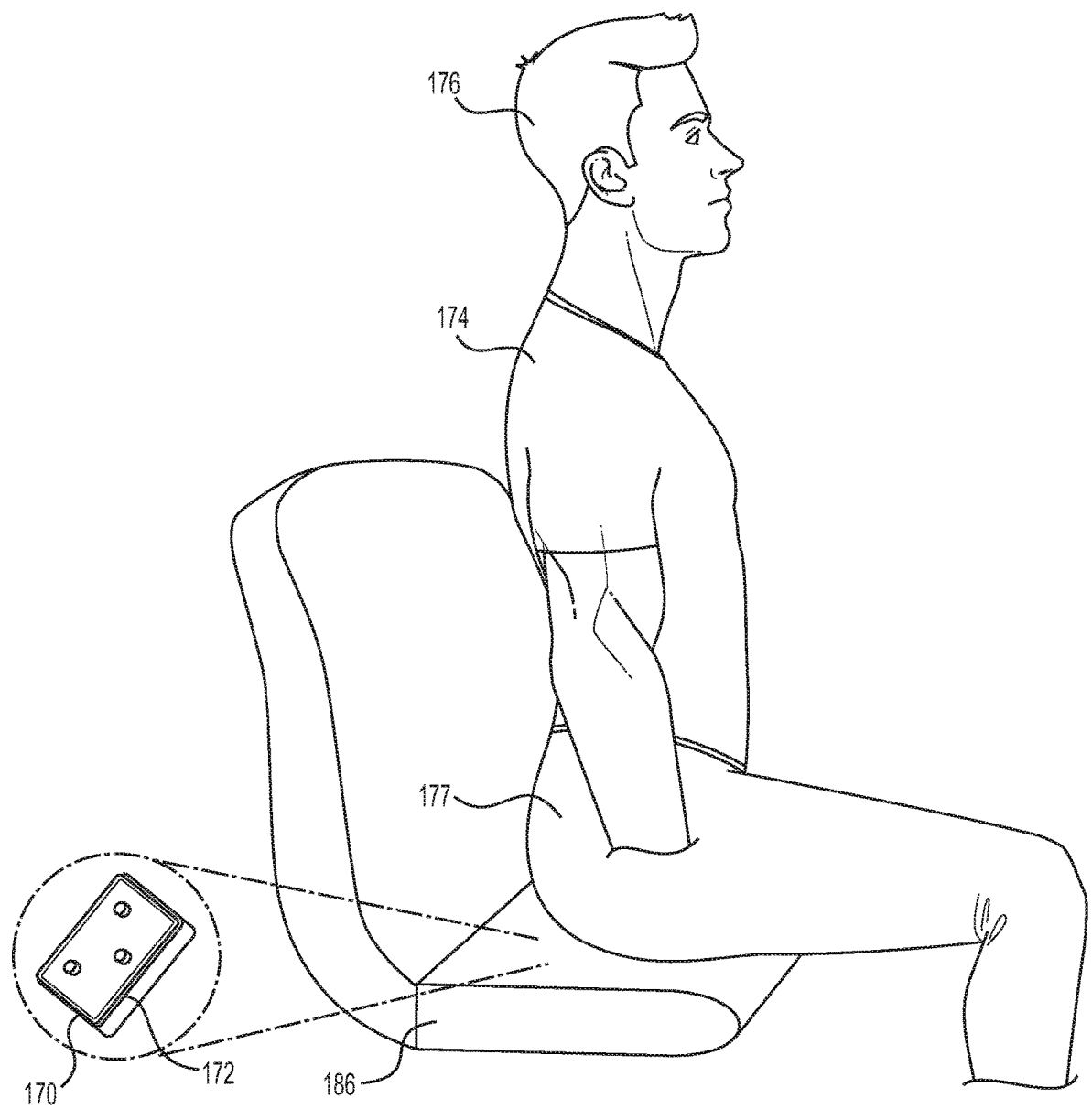
FIG. 10 illustrates a non-body contact directional EEG device according to an exemplary embodiment of the disclosure directed to a gluteus of a person without touching the skin of the person from a seat bottom.

FIG. 10 shows an example of using a non-body contact directional EEG device with a person through a seat, for example, of an automobile 186. In this embodiment, the sensors of the EEG device 170 are directed to detect signals from a gluteus 177 of the person 174.

Figure 11:
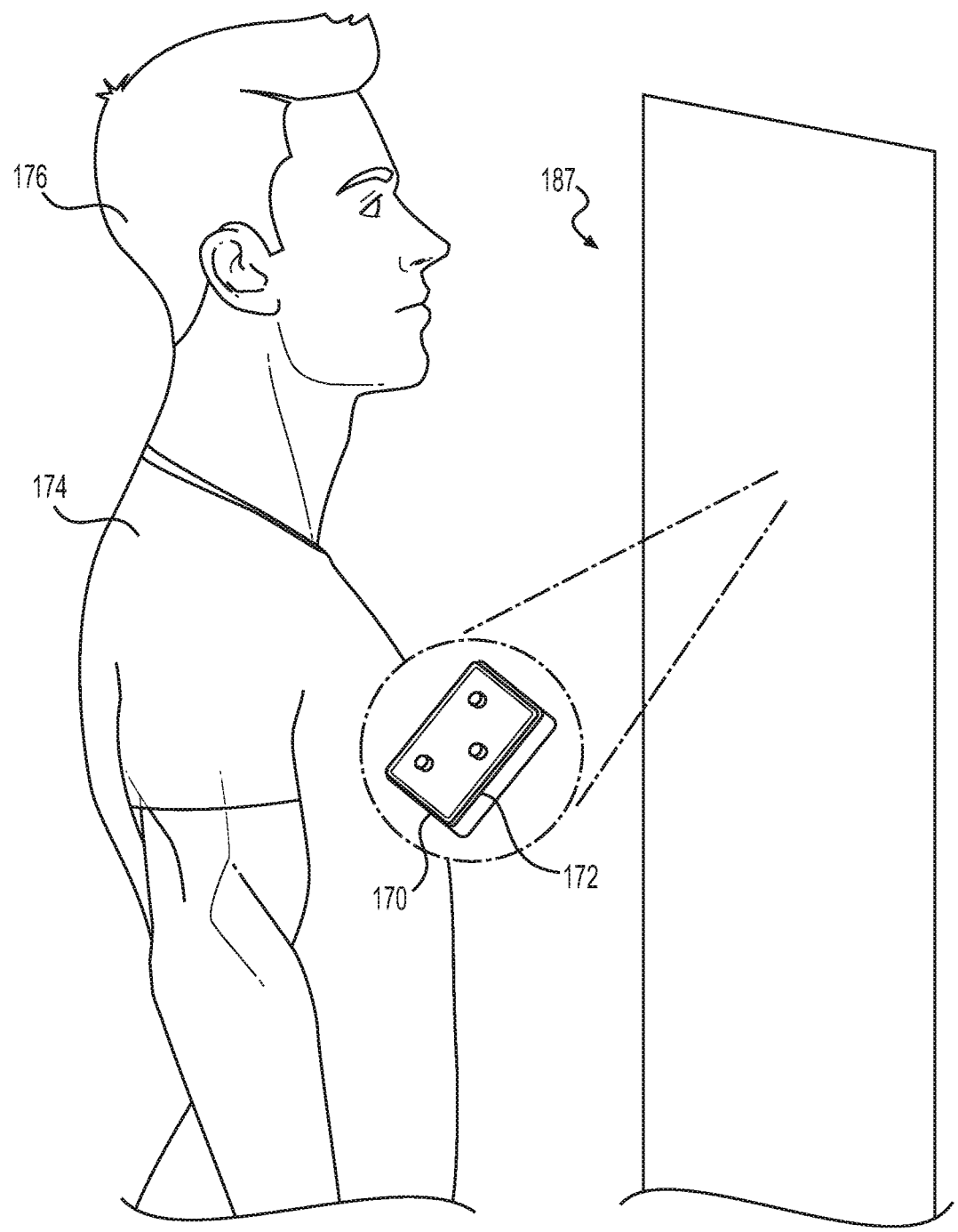
FIG. 11 illustrates a non-body contact directional EEG device according to an exemplary embodiment of the disclosure directed to a side of a person without touching the skin of the person from a stanchion.
Figure 12:
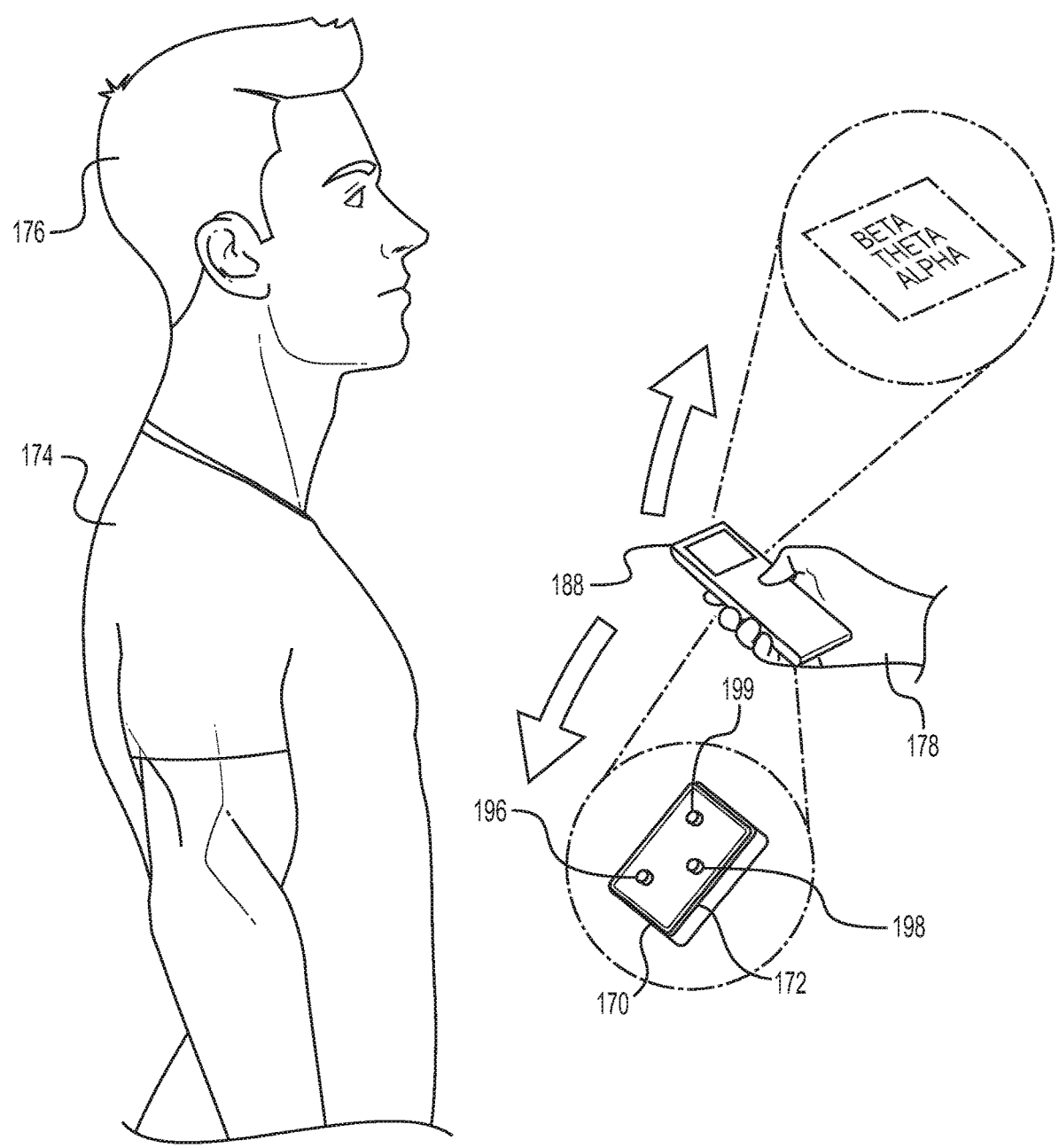
FIG. 12 illustrates a non-body contact directional EEG device according to an exemplary embodiment of the disclosure directed to anywhere on a body or head of a person without touching the skin of the person from a handheld device.

FIGS. 11 and 12 show examples of using a non-body contact directional EEG device with a person, according to the various embodiments of the disclosure.

In FIG. 11, the non-body contact directional EEG device 170 or at least the non-contact sensors 198 and 199 is configured for placement in proximity to a portion of the body of the person 174 below the head. The non-body contact directional EEG device 170 provides structural support for the amplifier and wireless transmitter unit 172, and more particularly takes the form of a stanchion 187 for placement near the body of a person 174 (FIG. 11).

In the exemplary embodiment of FIG. 12, the amplifier and wireless transmitter unit 172 can be either an integral part of the wireless handheld non-body contact directional EEG device, or a detachable element. On the inside surface handheld non-body contact directional EEG device 188 are a pair of non-contact sensors 198 and 199 corresponding to the non-contact sensors 26 and 28 described hereinabove with reference to FIG. 1. In FIG. 12, while no sensors are visible, they may be located on the inside surface of the handheld unit 188 at the general position of the amplifier and wireless transmitter unit 172. The sensors including the non-contact sensors 198 and 199 are electrically connected to the amplifier and wireless transmitter unit 172, and operate as described hereinabove with reference to FIG. 1. In operation, the non-contact sensors 198 and 199 are placed at least proximate to a portion of the person's 174 body below the head, and/or at the head 176 (FIG. 12).

In addition, the embodiment shown in FIG. 12 illustrates an alternative embodiment wherein all data collection, signal processing and analysis functions are implemented in a single self-contained unit placed proximate to either the body or head of the person. As represented by a display on the device 188 in FIG. 12, signal processing may be employed to determine and drive a display of the magnitude of brainwave activity in different brainwave frequency bands of interest. In FIG. 12, the display represents the magnitude of brainwave activity in the "theta," "alpha" and "beta" frequency bands. Alternatively, a single display of a person's level of attention or other measurements can be provided. In either case, auditory signaling or haptic response may also be employed to indicate when certain pre-programmed thresholds have been either exceeded or unattained, thus alerting the user that physiological change is necessary.

Figure 13A:
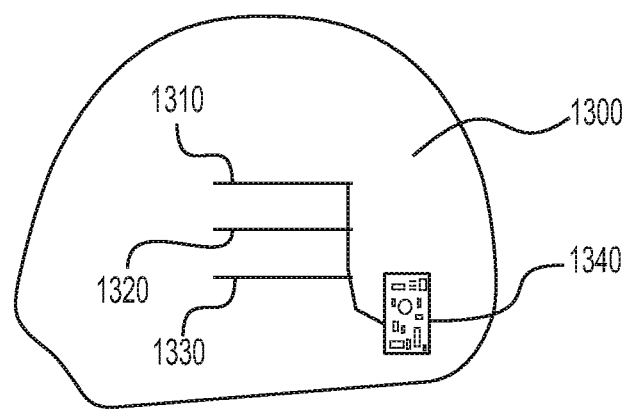
FIG. 13A illustrates an exemplary bar array sensor configuration for use with a non-body contact directional EEG device according to the disclosure.

FIG. 13A illustrates an exemplary three bar array configuration in which multiple non-contact sensors can be arranged. As shown, the sensors 1310, 1320 and 1330 are positioned as parallel bars within a headrest 1300 and coupled to the device 1340. Thus, as person sits down in the seat, their head would naturally be positioned adjacent to the headrest 1300, and thus the sensors 1310, 1320 and 1330. The headrest 1300 and bar array can be covered by a material that does not interfere with the sensors' 1310, 1320 and 1330 ability to detect. Of course, it should be understood that the bar array configuration of sensors 1310, 1320 and 1330 can be incorporated into any number of other items depending on the application.

Figure 13B:
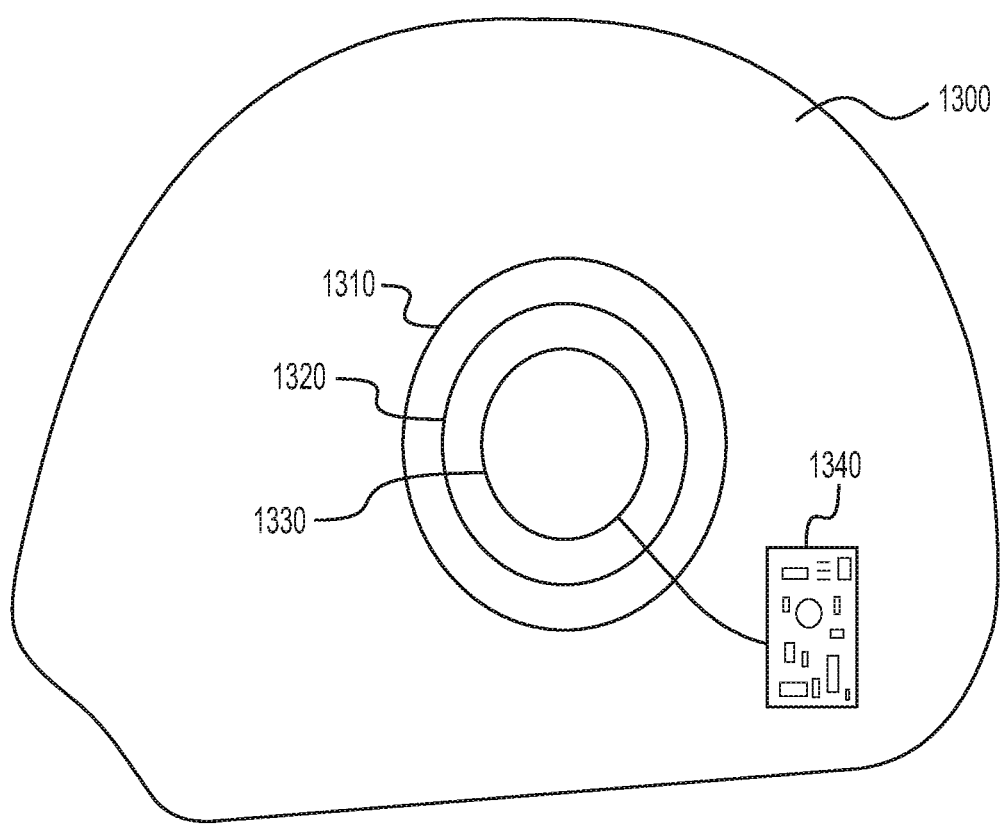
FIG. 13B illustrates an exemplary concentric rings array sensor configuration for use with a non-body contact directional EEG device according to the disclosure.

FIG. 13B illustrates an exemplary concentric ring array configuration in which multiple non-contact sensors can be arranged. As shown, the sensors 1310, 1320 and 1330 are arranged as concentric rings within a headrest 1300 of a seat and coupled to the device 1340. Thus, as person sits down in the seat, their head would naturally be positioned adjacent to the headrest 1300, and thus the sensors 1310, 1320 and 1330. Similar to the above, it should be understood that the concentric ring array configuration of sensors 1310, 1320 and 1330 can be covered and incorporated into any number of items depending on the application.

The concentric ring array configuration of the sensors 1310, 1320 and 1330 includes many benefit, including that the configuration can be highly directional. Thus, in addition to being able to aim the concentric ring array to a particular portion of a person's head or body, an orientation or movement of a person's head can be detected. The detected orientation or movement can then be further process in order to recognize the movement and possibly control other devices. Additionally, the concentric ring array configuration permits sensors to be densely placed in items, such as the headrest 1300. In the headrest 1300 example, more sensor material per square inch can result in an increase in the sensors' ability to detect raw signal from a person.

Figure 14A:
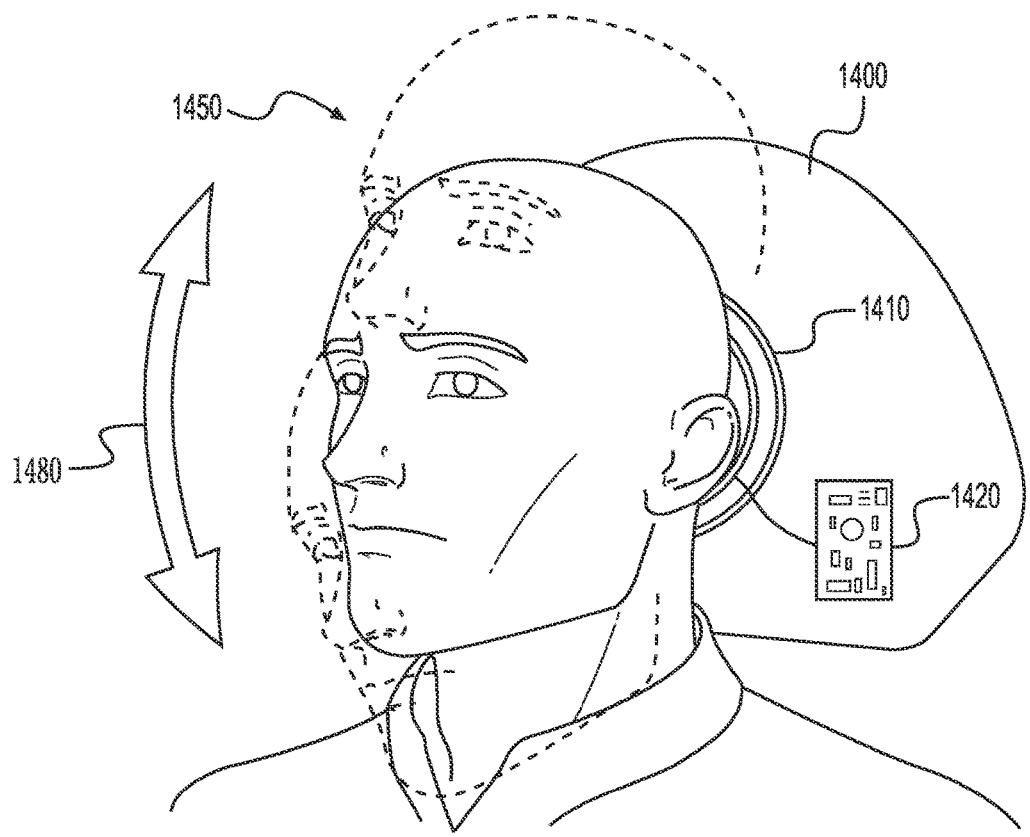
FIG. 14A illustrates an exemplary non-body contact directional EEG device that is positioned in proximity to a user.
Figure 14B:
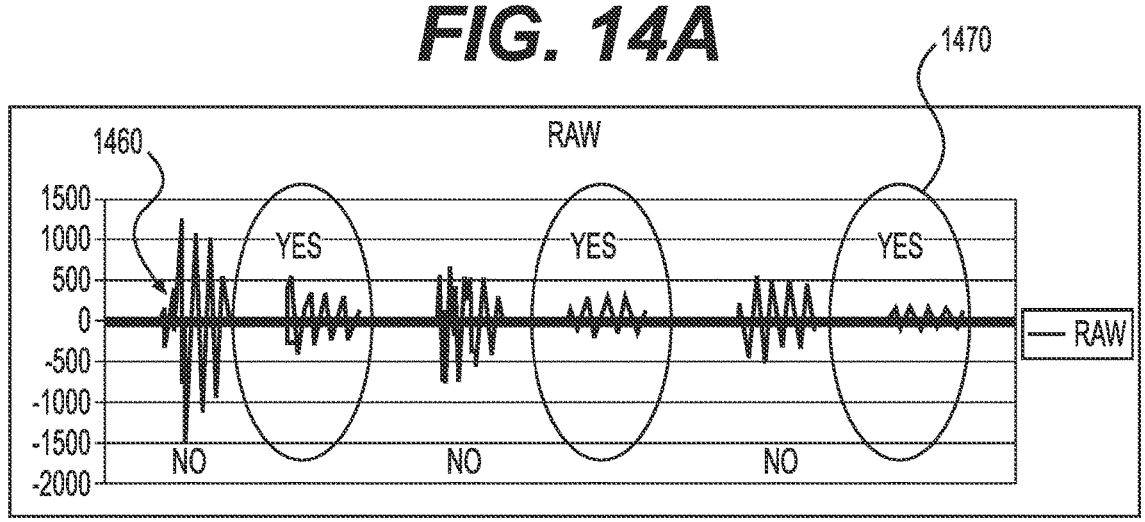
FIG. 14B illustrates an exemplary signal that can be detected by a non-body contact directional EEG device that is positioned in proximity to a user.

FIG. 14 A illustrates an exemplary non-body contact directional EEG device having at least sensors that are positioned in proximity to a person. In this example, a headrest 1400 is fitted with a concentric ring array configuration of sensors 1410. The sensors 1410 are coupled to a non-body contact directional EEG device that can be located either proximate to or remote from the sensors 1410. When a person 1450 sits, their head is positioned adjacent to the headrest 1400, and thus the sensor 1410 may detect raw brainwave activity signals from the person 1450.

As described above, the concentric ring array configuration of sensors 1410 can be directional in that a signal detected by the sensor 1410 can vary as an orientation of an object emitting signals, such as a person's head, changes. Accordingly, as the person 1450 nods their head in a "yes" motion (arrow 1480), the signal detected by the sensor 1410 can vary. Such specific movements of the head can cause a variation of the signal that can have a particular signature that the non-body contact directional EEG device 1420 can identify. In this example, the non-body contact directional EEG device 1420 can identify the signature of the signal as an affirmative gesture or response.

Once detected, the non-body contact directional EEG device 1420 can act or forward the detected response to another device to take subsequent action consistent with the gesture. For example, in an automotive setting, automation may ask a driver whether they would like to accept an incoming telephone call while driving. If the person 1450 responds with an affirmative gesture, then the call could be automatically connected; otherwise, the call could be declined.

FIG. 14 B shows an exemplary signal 1460 that can be detected by the sensor 1410. In this example, the signal 1460 can be processed to identify a signature pattern corresponding to a particular action of a person 1450 in proximity to the sensor 1410. As shown, portions of the signal 1460 corresponding an affirmative gesture or response described above are identified as a "Yes" action 1470. Again, once identified, the detected "Yes" action 1470 can be recorded and/or used to direct further events.

Figure 15A:
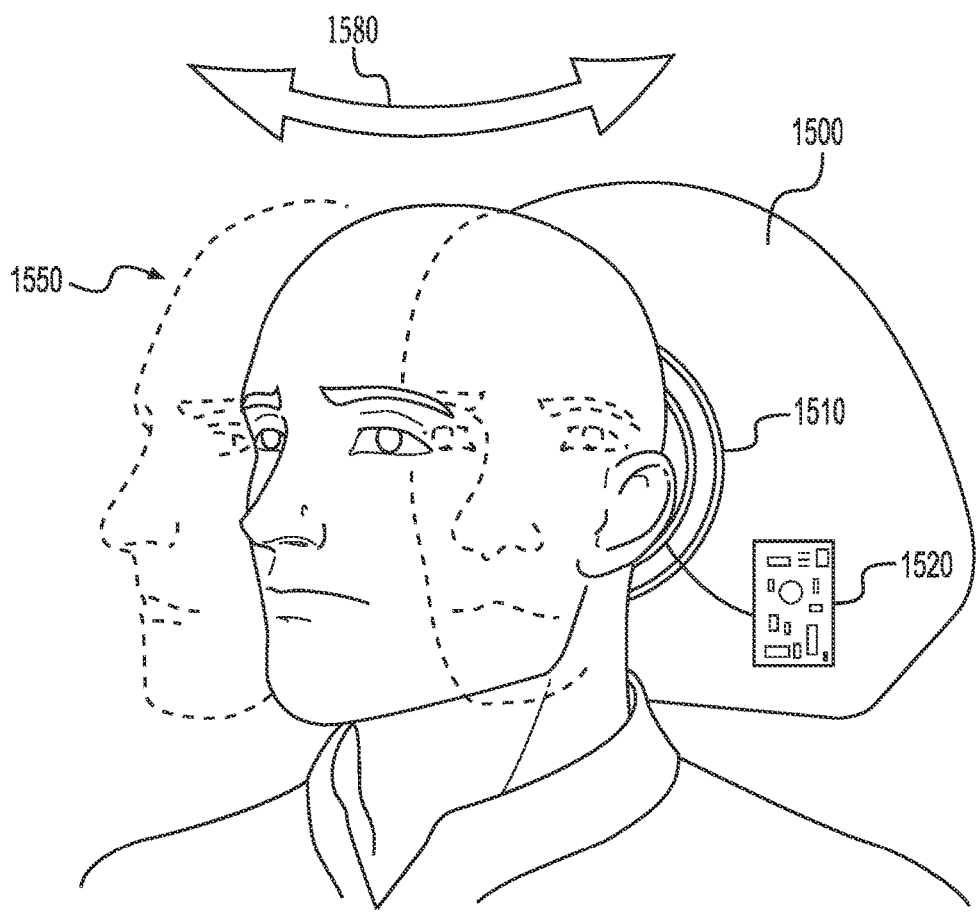
FIG. 15A illustrates an exemplary non-body contact directional EEG device that is positioned in proximity to a person.

In a similar manner to FIG. 14 A above, FIG. 15 A illustrates an exemplary non-body contact directional EEG device that is positioned in proximity to a person. Again, a headrest 1500 is fitted with a concentric ring array configuration of sensors 1510. The sensors 1510 are coupled to a non-body contact directional EEG device that can be located either proximate to or remote from the sensors 1510 that detect brainwave activity signals.

In this example, as the person 1550 moves their head in a "no" motion (arrow 1580), the signal detected by the sensor 1510 can vary. In this example, the non-body contact directional EEG device 1520 can identify a signature of the signal as a negative gesture or response.

Figure 15B:
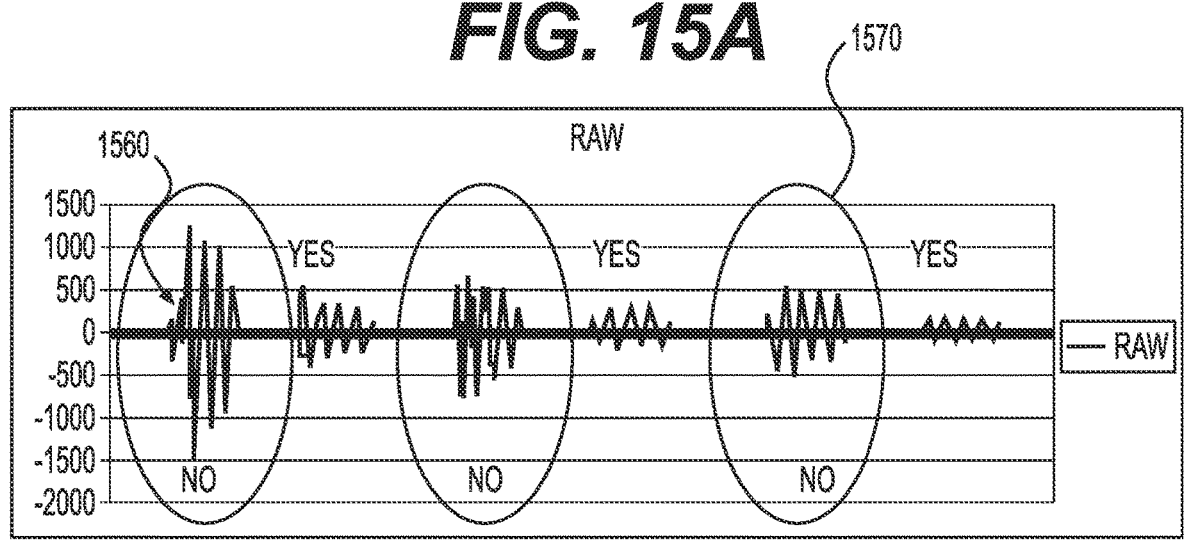
FIG. 15B illustrates an exemplary signal that can be detected by a non-body contact directional EEG device that is positioned in proximity to a user.

FIG. 15B shows an exemplary signal 1560 that can be detected by the sensor 1510. Again, the signal 1560 can be processed to identify a signature pattern corresponding to a particular action of a person. As shown, portions of the signal 1560 corresponding a negative gesture or response described above are identified as a "No" action 1570. Once identified, the detected "No" action 1570 can be recorded and/or used to direct further events.

Figure 16A:
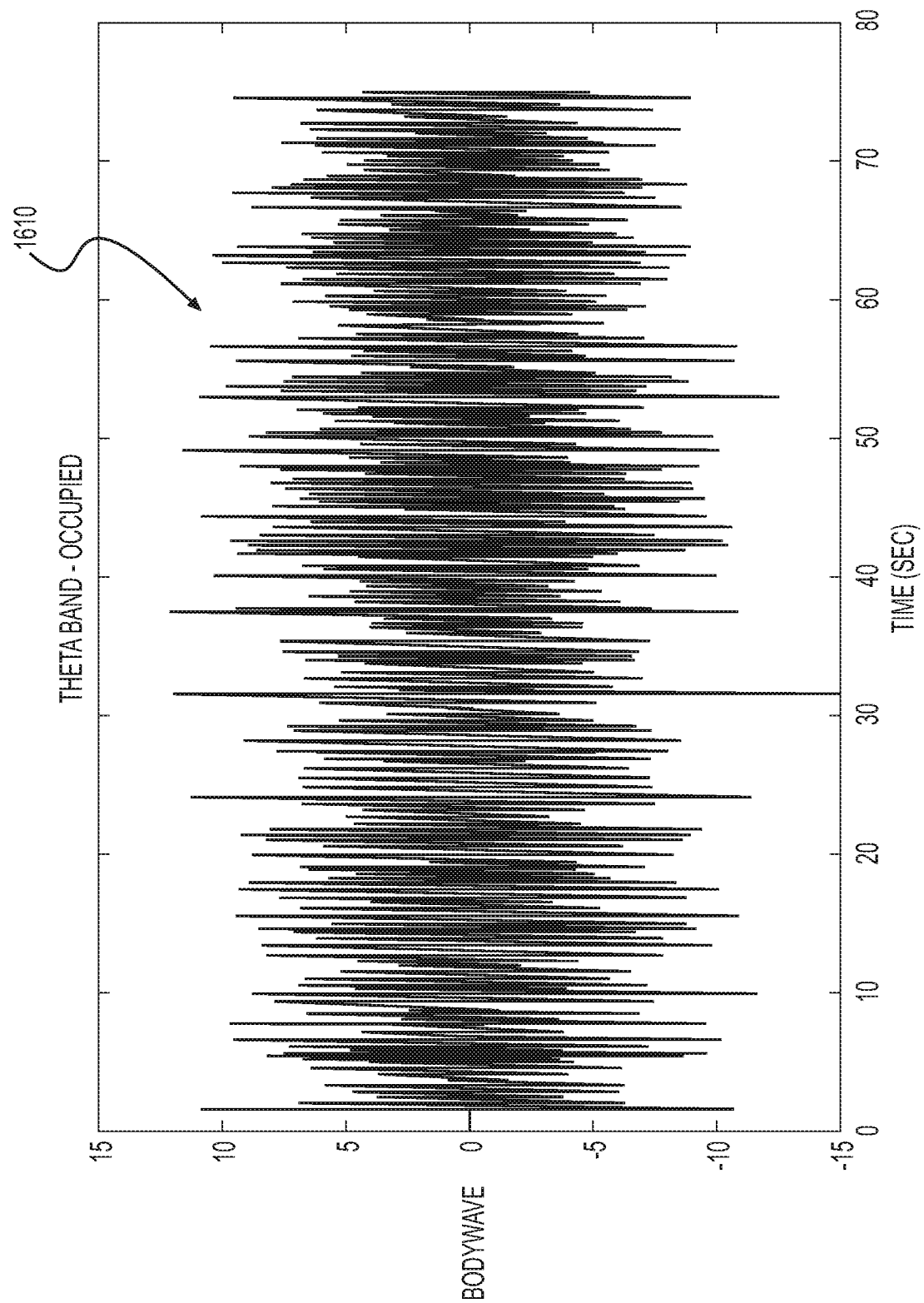
FIG. 16A shows exemplary signals detected by a non-body contact directional EEG device when a person is in proximity to the device.
Figure 16B:
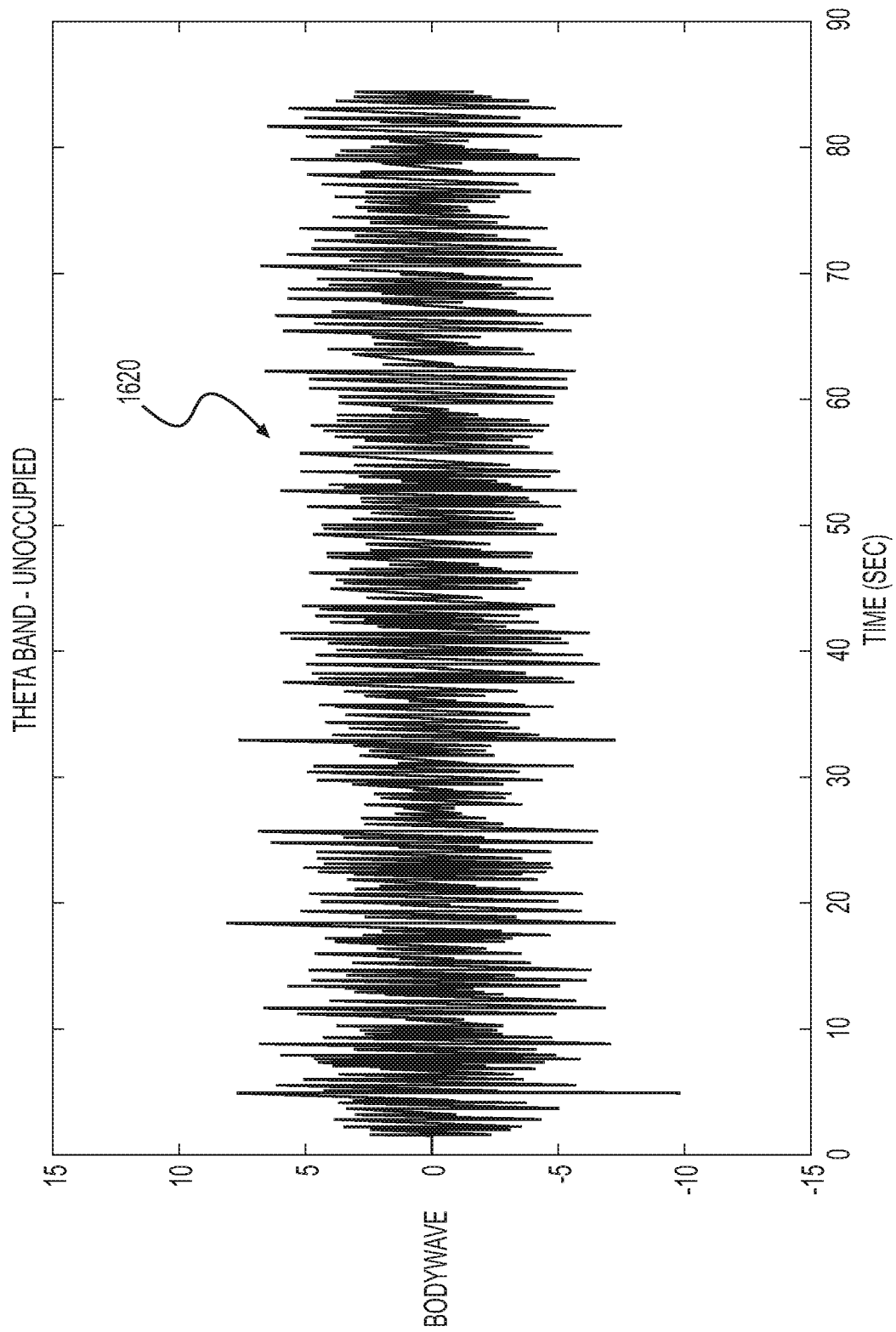
FIG. 16B shows exemplary signals detected by a non-body contact directional EEG device when a person is not in proximity to the device.

FIGS. 16 A and B show signals detected by a non-body contact directional EEG device when a person is in proximity or not in proximity to the device, respectively. Such detection can be useful to know whether a person is present in a space, such as sitting in a chair. For example, in FIG. 16A the detected signal 1610 (Theta Band) has a signature pattern that indicates that a person is present in proximity to a senor, while in FIG. 16B the detected signal 1620 has a different signature pattern that indicates that a person not in proximity to a senor. The differing signature patterns can differ in magnitude and/or frequency pattern and can be identified by the non-body contact directional EEG device. Once identified, they can be recorded and/or used to direct further events While specific embodiments of the invention have been illustrated and described herein, it is realized that numerous modifications and changes will occur to those skilled in the art. It is therefore to be understood that the appended claims are intended to cover all such modifications and changes as fall within the true spirit and scope of the invention.

What is claimed is:

1. A device for monitoring an electrical activity generated by a brain of a person, the device comprising:
   an array of a plurality of non-contact sensors, each of the non-contact sensors configured to detect electrical signals down to 100 nanovolts (nV) produced by the brain of the person without making a contact with the person, each of the non-contact sensors being attached to an external object that is configured to be non-wearable and separated from the person during use, wherein each of the non-contact sensors is at least one of a dry electrode or a contactless biopotential sensor, and wherein each of the non-contact sensors is disposed within the array to accommodate a plurality of different orientations of a head of the person,
   wherein each of the plurality of non-contact sensors in the array is configured to detect the electrical signals within different frequency bands including a delta band having a frequency up to 3 Hz, a theta band having a frequency between 4 Hz and 8 Hz, an alpha band having a frequency between 12 Hz and 30 Hz, and a gamma band having a frequency between 26 Hz and 100 Hz, and
   wherein the array of the plurality of non-contact sensors is configured to detect the electrical signals from 10 to 20 inches away from the person; and
   an amplifying device coupled to the array of the plurality of the non-contact sensors that is configured to generate analysis signals corresponding to the electrical signals produced by the brain of the person by attenuating frequency components of the detected electrical signals that are unrelated to the analysis signals, while amplifying frequency components of the detected electrical signals that are related to the analysis signals, wherein the amplifying device includes:
      a high pass filter that is coupled to the array of the plurality of the non-contact sensors, the high pass filter configured to generate a first filtered signal,
      a first amplifier that is configured to receive the first filtered signal from the high pass filter and generate a first amplified signal,
      a second amplifier that is configured to receive the first amplified signal from the first amplifier and generate a second amplified signal,
      a low pass filter that is configured to receive the second amplified signal from the second amplifier and generate a second filtered signal,
      a third amplifier that is configured to receive the second filtered signal from the low pass filter and generate the analysis signals, and
      an analog-to-digital convertor that is configured to receive the analysis signals from the third amplifier and digitize the analysis signals.

2. The device according to claim 1, further comprising:
   a processor that is configured to analyze the analysis signals to detect patterns in the analysis signals corresponding to a state of the person.

3. The device according to claim 2, wherein the state of the person includes at least one of an emotional state, a cognitive load state, a cognitive state, and an alertness state of the person, and
   wherein the processor is configured to determine the state of the person based on the detected electrical signals within the different frequency bands.

4. The device according to claim 3, wherein the processor is further configured to control other devices based on the determined state of the person.

5. The device according to claim 2, wherein when the processor detects a pattern corresponding to a predetermined state of the person, the processor transmits an action signal to another device to take a subsequent action.

6. The device according to claim 1, further comprising:
   a processor that is configured to analyze the analysis signals to detect patterns in the analysis signals corresponding to an activity of the person.

7. The device according to claim 6, wherein the activity of the person includes moving the head of the person in an affirmative gesture or a negative gesture.

8. The device according to claim 6, wherein the activity of the person includes moving the head or a body of the person so that the device detects whether a space monitored by the non-contact sensors is occupied or unoccupied, respectively, by the person.

9. The device according to claim 6, wherein when the processor detects the patterns corresponding to the activity of the person, the processor transmits an action signal to another device to take a subsequent action.

10. The device according to claim 1, wherein the non-contact sensors are located remotely from the head of the person, but are located adjacent to at least one of a neck, back, and gluteus of the person.

11. The device according to claim 1, wherein the non-contact sensors are configured in at least one of a bar configuration and a concentric ring configuration.

12. The device according to claim 1, wherein the high pass filter is configured to generate the first filtered signal by attenuating frequency components of the detected electrical signals, the attenuated frequency components being lower than a first cutoff frequency.

13. The device according to claim 12, wherein the first amplifier is configured to generate the first amplified signal by amplifying components of the first filtered signal that are related to the analysis signals.

14. The device according to claim 13, wherein the second amplifier is configured to generate the second amplified signal by amplifying the components of the first filtered signal that are related to the analysis signals.

15. The device according to claim 14, wherein the low pass filter is configured to generate the second filtered signal by attenuating frequency components of the second amplified signal, the attenuated frequency components being higher than a second cutoff frequency.

16. The device according to claim 15, wherein the third amplifier is configured to generate the analysis signals by amplifying components of the second filtered signal that are related to the analysis signals.

17. The device according to claim 1, wherein the low pass filter is an antialiasing filter that is an 8th order low pass filter implemented with a monolithic switched capacitor device.

18. The device according to claim 1, further comprising five or six arrays of the plurality of the non-contact sensors.

19. The device according to claim 1, wherein the first amplifier is a single stage amplifier with an average gain of 73, the second amplifier is an operational amplifier with an average gain of 101, and the third amplifier is an amplifier with an average gain of 2.

20. The device according to claim 1, wherein the processor is further configured to determine a direction of the head of the person based on a variation of signal strength detected by the array according to a position of the head of the person.

21. A method for monitoring electrical activity generated by a brain, the method comprising:
    detecting, by an array of a plurality of non-contact sensors, electrical signals down to 100 nanovolts (nV) produced by the brain of a person without making a contact with the person, the non-contact sensors being attached to an external object that is configured to be non-wearable and separated from the person during use, wherein each of the non-contact sensors is at least one of a dry electrode or a contactless biopotential sensor, and wherein each of the non-contact sensors is disposed within the array to accommodate a plurality of different orientations of a head of the person;
    detecting, by each of the plurality of non-contact sensors in the array, the electrical signals within different frequency bands including a delta band having a frequency up to 3 Hz, a theta band having a frequency between 4 Hz and 8 Hz, an alpha band having a frequency between 12 Hz and 30 Hz, and a gamma band having a frequency between 26 Hz and 100 Hz;
    detecting, by the array of the plurality of non-contact sensors, the electrical signals from 10 to 20 inches away from the person;
    generating, by an amplifying device coupled to the array of the plurality of the non-contact sensors, analysis signals corresponding to the electrical signals produced by the brain of the person by attenuating frequency components of the detected electrical signals that are unrelated to the analysis signals, while amplifying frequency components of the detected electrical signals that are related to the analysis signals;
    generating a first filtered signal by a high pass filter that is coupled to the array of the plurality of the non-contact sensors;
    receiving the first filtered signal from the high pass filter, and generating a first amplified signal by a first amplifier;
    receiving the first amplified signal from the first amplifier and generating a second amplified signal by a second amplifier;
    receiving the second amplified signal from the second amplifier and generating a second filtered signal by a low pass filter;
    receiving the second filtered signal from the low pass filter and generating the analysis signals by a third amplifier; and
    receiving the analysis signals from the third amplifier and digitizing the analysis signals by an analog-to-digital convertor.

22. The method of claim 21, which comprises placing the non-contact sensors toward the head or a body of the person from a distance without physically touching the person.

23. The method of claim 21, wherein the attenuating frequency components comprises filtering, by the low pass filter, an analysis signal portion having frequency components relevant to a brain electrical activity from the detected electrical signals by attenuating unrelated frequency components.

24. The method of claim 23, wherein the low pass filter has a cutoff frequency within a range of 20 Hz to 40 Hz.

25. The method of claim 23, further comprising:
    adaptively determining heart rate signals of the person from the detected electrical signals, wherein the analysis signal portion is filtered to produce the analysis signals including the frequency components relevant to the brain electrical activity while attenuating the unrelated frequency components by employing the determined heart rate signals to actively cancel heart rate signal components from the detected electrical signals.

26. A non-transitory computer readable medium storing computer readable instructions thereon that, when executed by a computer, causes the computer to perform a method for monitoring a physiological state of a person having a body including a head, the method comprising:
    detecting, by an array of a plurality of non-contact sensors, electrical signals down to 100 nanovolts (nV) produced by a brain of the person without making a contact with the person, the non-contact sensors being attached to an external object that is configured to be non-wearable and separated from the person during use, wherein each of the non-contact sensors is at least one of a dry electrode or a contactless biopotential sensor, and wherein each of the non-contact sensors is disposed within the array to accommodate a plurality of different orientations of the head of the person;
    detecting, by each of the plurality of non-contact sensors in the array, the electrical signals within different frequency bands including a delta band having a frequency up to 3 Hz, a theta band having a frequency between 4 Hz and 8 Hz, an alpha band having a frequency between 12 Hz and 30 Hz, and a gamma band having a frequency between 26 Hz and 100 Hz;
    detecting, by the array of the plurality of non-contact sensors, the electrical signals from 10 to 20 inches away from the person;
    generating, by an amplifying device coupled to the array of the plurality of the non-contact sensors, analysis signals corresponding to the electrical signals produced by the brain of the person by attenuating frequency components of the detected electrical signals that are unrelated to the analysis signals, while amplifying frequency components of the detected electrical signals that are related to the analysis signals;

generating a first filtered signal by a high pass filter that is coupled to the array of the plurality of the non-contact sensors;

receiving the first filtered signal from the high pass filter, and generating a first amplified signal by a first amplifier;

receiving the first amplified signal from the first amplifier and generating a second amplified signal by a second amplifier;

receiving the second amplified signal from the second amplifier and generating a second filtered signal by a low pass filter;

receiving the second filtered signal from the low pass filter and generating the analysis signals by a third amplifier; and receiving the analysis signals from the third amplifier and digitizing the analysis signals by an analog-to-digital convertor.

27. The method of claim 26, further comprising:

processing the detected electrical signals to produce at least one bandpass filtered state indicating a signal representative of a magnitude within a predetermined frequency range as an indication of the physiological state of the person, wherein the at least one bandpass filtered state indicating the signal is an intention indicating signal and the method further comprises processing the detected electrical signals to produce at least one bandpass filtered attention indicating another signal representative of another magnitude within another predetermined frequency range as an indication of the person's level of attention.

28. The method of claim 27, wherein processing the detected electrical signals to produce the at least one bandpass filtered state indicating the signal representative of the magnitude within the predetermined frequency range as the indication of the physiological state of the person further comprises:

bandpass filtering the detected electrical signals to produce bandpass limited signals within the predetermined frequency range; and analyzing the bandpass limited signals to determine the magnitude as the at least one bandpass filtered state indicating the signal.

29. The method of claim 28, wherein bandpass filtering the electrical signals includes applying the low pass filter ahead of a bandpass filter.

30. The method of claim 27, further comprising:

actively determining heart rate signals of the person from the detected electrical signals wherein processing the detected electrical signals to produce the at least one bandpass filtered state indicating the signal representative of the magnitude within the predetermined frequency range as the indication of the physiological state of the person comprises employing the determined heart rate signals to actively attenuate heart rate signal components from the detected electrical signals.

\* \* \* \* \*